(12) United States Patent
Becker et al.

(10) Patent No.: US 7,390,791 B2
(45) Date of Patent: Jun. 24, 2008

(54) PRODRUGS OF PHOSPHONATE NUCLEOTIDE ANALOGUES

(75) Inventors: Mark W. Becker, Belmont, CA (US); Harlan H. Chapman, La Honda, CA (US); Tomas Cihlar, Foster City, CA (US); Eugene J. Eisenberg, San Carlos, CA (US); Gong-Xin He, Fremont, CA (US); Michael R. Kernan, Pacifica, CA (US); William A. Lee, Los Altos, CA (US); Ernest J. Prisbe, Los Altos, CA (US); John C. Rohloff, Mountain View, CA (US); Mark L. Sparacino, Morgan Hill, CA (US)

(73) Assignee: Gilead Sciences, Inc., Foster City, CA (US)

( * ) Notice: Subject to any disclaimer, the term of this patent is extended or adjusted under 35 U.S.C. 154(b) by 291 days.

(21) Appl. No.: 10/798,692

(22) Filed: Mar. 11, 2004

(65) Prior Publication Data

US 2005/0009043 A1 Jan. 13, 2005

Related U.S. Application Data

(63) Continuation of application No. 10/354,207, filed on Jan. 28, 2003, now abandoned, which is a continuation of application No. 09/909,560, filed on Jul. 20, 2001, now abandoned.

(60) Provisional application No. 60/220,021, filed on Jul. 21, 2000.

(51) Int. Cl.
*A01N 43/48* (2006.01)
*A61K 3/1675* (2006.01)
*C07F 9/6512* (2006.01)

(52) U.S. Cl. .................................. 514/44; 514/7; 514/81
(58) Field of Classification Search ............... 435/4, 435/7.1, 9.1; 514/44, 7, 81, 85
See application file for complete search history.

(56) References Cited

U.S. PATENT DOCUMENTS

| | | | |
|---|---|---|---|
| 5,053,215 A | 10/1991 | Rand et al. | |
| 5,413,996 A | 5/1995 | Bodor | |
| 5,591,851 A | 1/1997 | Alexander | |
| 5,624,894 A | 4/1997 | Bodor | |
| 5,627,165 A | 5/1997 | Glazier | |
| 5,656,745 A | 8/1997 | Bischofberger et al. | |
| 5,663,159 A | 9/1997 | Starrett, Jr. et al. | |
| 5,717,095 A | 2/1998 | Arimilli et al. | |
| 5,756,486 A | 5/1998 | Alexander et al. | |
| 5,792,756 A | 8/1998 | Starrett, Jr. et al. | |
| 5,798,340 A | 8/1998 | Bischofberger et al. | |
| 5,886,179 A | 3/1999 | Arimilli et al. | |
| 5,977,061 A | 11/1999 | Holy et al. | |
| 5,977,089 A | 11/1999 | Arimilli et al. | |
| 6,169,078 B1 | 1/2001 | Hughes et al. | |
| 6,225,460 B1 | 5/2001 | Bischofberger et al. | |
| 6,245,750 B1 | 6/2001 | Shepard | |
| 6,339,151 B1 | 1/2002 | Shepard et al. | |
| 6,348,185 B1 | 2/2002 | Piwnica-Worms | |
| 6,355,629 B2 | 3/2002 | Kozak | |
| 6,436,437 B1 | 8/2002 | Yatvin et al. | |
| 2001/0031873 A1 | 10/2001 | Greenwald et al. | |
| 2001/0034440 A1 | 10/2001 | Shepard et al. | |
| 2002/0120100 A1 | 8/2002 | Bonny | |

FOREIGN PATENT DOCUMENTS

| | | |
|---|---|---|
| EP | 0 336 364 A2 | 10/1989 |
| EP | 0 481 214 A1 * | 4/1992 |
| WO | WO 95/07920 | 3/1995 |
| WO | WO 96/29336 | 9/1996 |
| WO | WO 96/33200 | 10/1996 |
| WO | WO 96/37503 | 11/1996 |
| WO | WO 97/24361 | 7/1997 |
| WO | WO 99/37753 | 7/1999 |
| WO | WO 00/18775 | 4/2000 |
| WO | WO 0208241 A2 * | 1/2002 |

OTHER PUBLICATIONS

Aarons et al., "Pharmacokinetic Evaluation of Site-Specific Drug Delivery Systems", 12:121-126, Novel Drug Delivery and Its Therapeutic Application (John Wiley & Sons), 1989.
Banerjee et al., "Design of Prodrugs Based on Enzyme-Substrate Specificity", Chapter 2, pp. 118-121, Design of Prodrugs, 1985.

(Continued)

*Primary Examiner*—Jon Weber
*Assistant Examiner*—Kailash Srivastava
(74) *Attorney, Agent, or Firm*—Max D. Hensley

(57) ABSTRACT

A novel method has led to the identification of novel mixed ester-amidates of PMPA for retroviral or hepadnaviral therapy, including compounds of structure (5a)

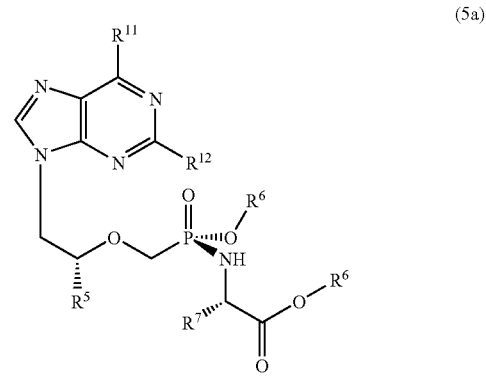

having substituent groups as defined herein. Compositions of these novel compounds in pharmaceutically acceptable excipients and their use in therapy and prophylaxis are provided.

13 Claims, 3 Drawing Sheets

OTHER PUBLICATIONS

Brunel et al., "A Practical Method for the Large-Scale Synthesis of Diastereomerically Pure (2R,5S)-3-Phenyl-2-(8-quinolinoxy)-1,3-diaza-2-phosphabicyclo-[3.3.0]-octane Ligand (QUIPHOS)", 64:8940-8942, J Org Chem, 1999.

Bundgaard, H., "Design of Prodrugs: Bioreversible Derivatives for Various Functional Groups and Chemical Entities", Chapter 1, pp. 70-92, Design of Prodrugs, 1985.

Chapman et al., "Practical Synthesis, Separation, and Stereochemical Assignment of the PMPA Pro-Drug GS-7340", 20(4-7):621-628, Nucleosides, Nucleotides & Nucleic Acids, 2001.

Connors, T.A., "Prodrugs in Cancer Chemotherapy", Chapter 9, pp. 291-316, Design of Prodrugs, 1985.

Jones, Geraint, "Decreased Toxicity and Adverse Reactions via Prodrugs", Chapter 6:pp. 199-241, Design of Prodrugs, 1985.

Kumar et al., "Heterocalixarenes. 1. Calix[2]uracil[2]arene: Synthesis, X-ray Structure, Conformational Analysis, and Binding Character", 64:7717-7726, J Org Chem, 1999.

McGuigan et al., "Aryl phosphate derivatives of AZT retain activity against HIV1 in cell lines which are resistant to the action of AZT", 17:311-321, Antiviral Res, 1992.

McGuigan et al., "Aryl Phosphate Derivatives of AZT Inhibit HIV Replication in Cells Where the Nucleoside is Poorly Active", 2(7):701-704, Bioorg Med Chem Lett, 1992.

McGuigan et al., "Certain phosphoramidate derivatives of dideoxy uridine (ddU) are active against HIV and successfully by-pass thymidine kinase", 351:11-14, FEBS, 1994.

McGuigan et al., "Intracellular Delivery of Bioactive AZT Nucleotides by Aryl Phosphate Derivatives of AZT", 36:1048-1052, J Med Chem, 1993.

McGuigan et al., "Phosphoramidates as potent prodrugs of anti-HIV nucleotides: studies in the amino region", 7(1):31-36, Antiviral Chem & Chemo, 1996.

Notari, Robert E., "Pharmacokinetic Aspects of Prodrug Design and Evaluation", Chapter 3, pp. 135-156, Design of Prodrugs, 1985.

Oliyai et al., "Aryl Ester Prodrugs of Cyclic HPMPC. I: Physicochemical Characterization and In Vitro Biological Stability", 16(11):1687-1693, Pharm Res, 1999.

Siddiqui et al., "Design and Synthesis of Lipophillic Phosphoramidate d4T-MP Prodrugs Expressing High Potency Against HIV in Cell Culture: Structural Determinants for in Vitro Activity and QSAR", 42:4122-4128, Pharm Res, 1999.

Starrett et al., "Synthesis, Oral Bioavailability Determination, and in Vitro Evaluation of Prodrugs of the Antiviral Agent 9-[2-(Phosphonomethoxy)ethyl]adenine (PMEA)", 37:1857-1864, J Med Chem, 1994.

Stella et al., "Site-Specific Drug Delivery via Prodrugs", Chapter 5, pp. 177-198, Design of Prodrugs, 1985.

Stella, Valentino J., "Prodrugs and Site-Specific Drug Delivery", 23(12):1275-1282, J Med Chem, Dec. 1980.

Strube et al., "Comparison of Batch Elution and Continuous Simulated Moving Bed Chromatography", 2:305-319, Organic Process Research & Development, 1998.

* cited by examiner

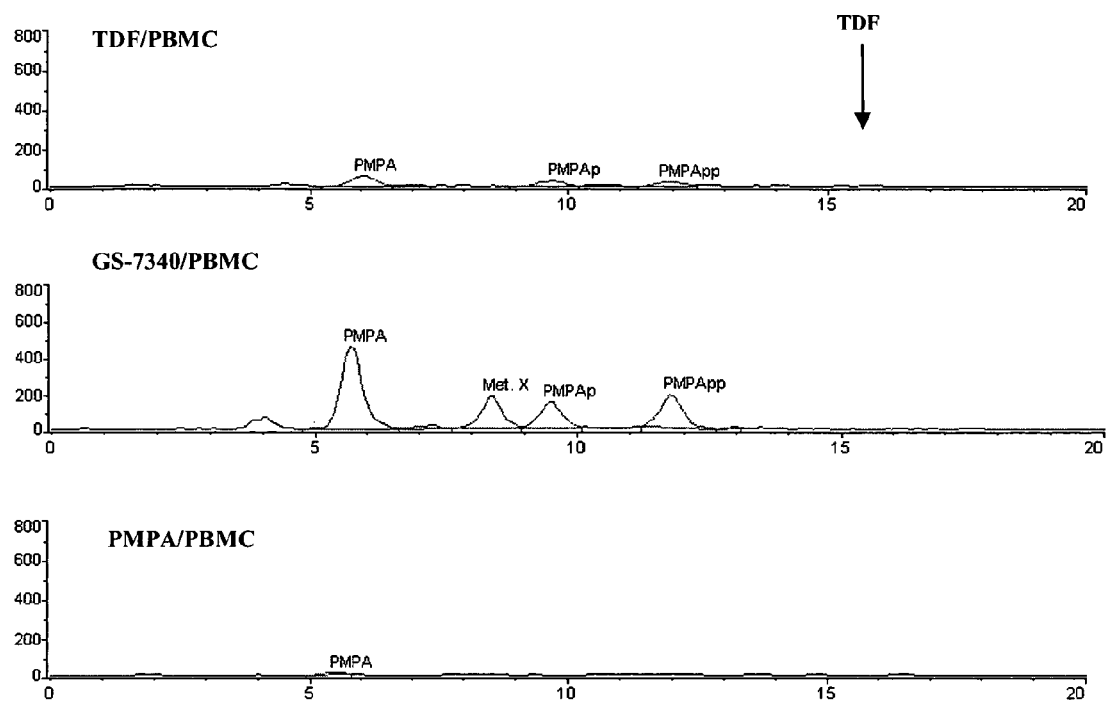
Figure 1. HPLC/C-14 Traces of PBMC Extracts from Human Blood Incubated for 1 h at 37°C with TDF, GS-7340 or PMPA.

Figure 2. PMPA and Prodrug Concentration in Plasma and PBMCs Following Oral Administration of GS 7340-2 to Dogs at 10 mg-eq/kg.
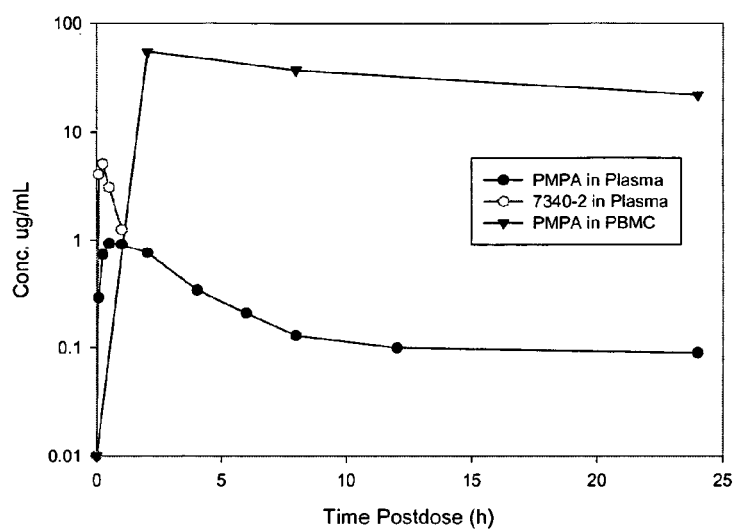

Figure 3. Depicts Tenofovir Exposure in PBMCs and Plasma Upon Administration of 10 mg-eq/kg in dogs
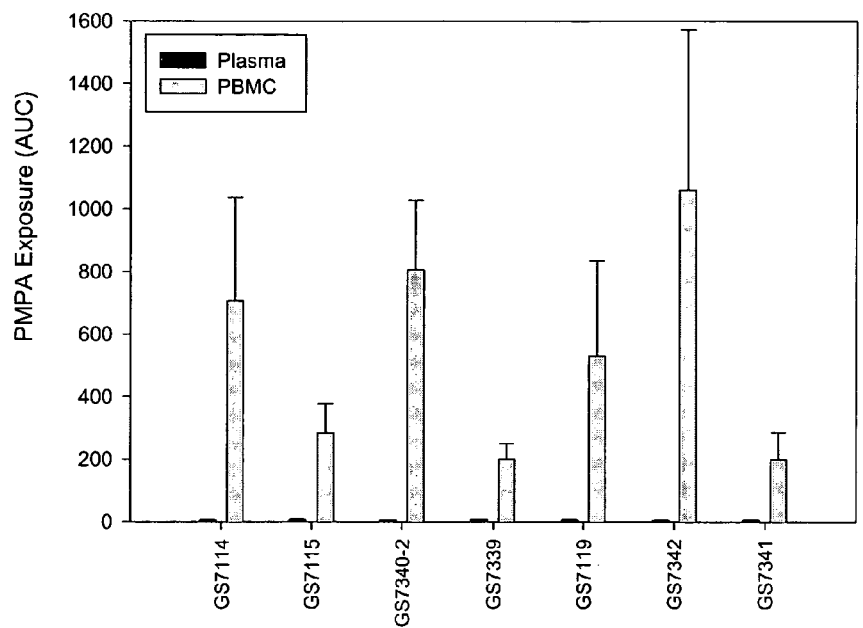

PRODRUGS OF PHOSPHONATE NUCLEOTIDE ANALOGUES

This non-provisional application is a continuation application of application Ser. No. 10/354,207, filed Jan. 28, 2003, now abandoned, which is a continuation application of application Ser. No. 09/909,560, filed Jul. 20, 2001, now abandoned, which is a regular utility application of provisional application 60/220,021, filed Jul. 21, 2000, now abandoned, all of which are incorporated herein by reference.

This application relates to prodrugs of methoxyphosphonate nucleotide analogues. In particular it relates to improved methods for making and identifying such prodrugs.

Many methoxyphosphonate nucleotide analogues are known. In general, such compounds have the structure A-OCH$_2$P(O)(OR)$_2$ where A is the residue of a nucleoside analogue and R independently is hydrogen or various protecting or prodrug functionalities. See U.S. Pat. Nos. 5,663,159, 5,977,061 and 5,798,340, Oliyai et al, "Pharmaceutical Research" 16(11):1687-1693 (1999), Stella et al., "J. Med. Chem." 23(12):1275-1282 (1980), Aarons, L., Boddy, A. and Petrak, K. (1989) *Novel Drug Delivery and Its Therapeutic Application* (Prescott, L. F. and Nimmo, W. S., ed.), pp. 121-126; Bundgaard, H. (1985) *Design of Prodrugs* (Bundgaard, H., ed.) pp. 70-74 and 79-92; Banerjee, P. K. and Amidon, G. L. (1985) *Design of Prodrugs* (Bundgaard, H., ed.) pp. 118-121; Notari, R. E. (1985) *Design of Prodrugs* (Bundgaard, H., ed.) pp. 135-156; Stella, V. J. and Himmelstein, K. J. (1985) *Design of Prodrugs* (Bundgaard, H., ed.) pp. 177-198; Jones, G. (1985) *Design of Prodrugs* (Bundgaard, H., ed.) pp. 199-241; Connors, T. A. (1985) *Design of Prodrugs* (Bundgaard, H., ed.) pp. 291-316. All literature and patent citations herein are expressly incorporated by reference.

SUMMARY OF THE INVENTION

Prodrugs of methoxyphosphonate nucleotide analogues intended for antiviral or antitumor therapy, while known, traditionally have been selected for their systemic effect. For example, such prodrugs have been selected for enhanced bioavailability, i.e., ability to be absorbed from the gastrointestinal tract and converted rapidly to parent drug to ensure that the parent drug is available to all tissues. However, applicants now have found that it is possible to select prodrugs that become enriched at therapeutic sites, as illustrated by the studies described herein where the analogues are enriched at localized focal sites of HIV infection. The objective of this invention is, among other advantages, to produce less toxicity to bystander tissues and greater potency of the parental drug in tissues which are the targets of therapy with the parent methoxyphosphonate nucleotide analogue.

Accordingly, pursuant to these observations, a screening method is provided for identifying a methoxyphosphonate nucleotide analogue prodrug conferring enhanced activity in a target tissue comprising:
(a) providing at least one of said prodrugs;
(b) selecting at least one therapeutic target tissue and at least one non-target tissue;
(c) administering the prodrug to the target tissue and to said at least one non-target tissue; and
(d) determining the relative antiviral activity conferred by the prodrug in the tissues in step (c).

In preferred embodiments, the target tissue are sites where HIV is actively replicated and/or which serve as an HIV reservoir, and the non-target tissue is an intact animal. Unexpectedly, we found that selecting lymphoid tissue as the target tissue for the practice of this method for HIV led to identification of prodrugs that enhance the delivery of active drug to such tissues.

A preferred compound of this invention, which has been identified by this method has the structure (1),

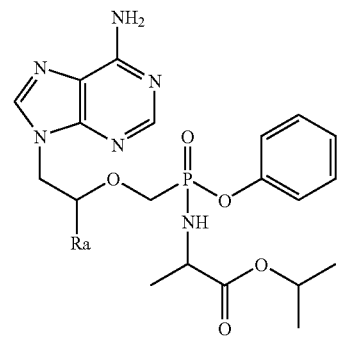

(1)

where Ra is H or methyl,
and chirally enriched compositions thereof, salts, their free base and solvates thereof.

A preferred compound of this invention has the structure (2)

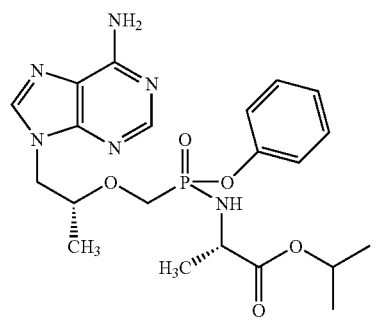

(2)

and its enriched diasteromers, salts, free base and solvates.

In addition, we unexpectedly found that the chirality of substituents on the phosphorous atom and/or the amidate substituent are influential in the enrichment observed in the practice of this invention. Thus, in another embodiment of this invention, we provide diastereomerically enriched compounds of this invention having the structure (3)

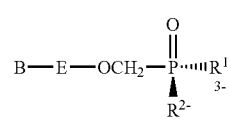

(3)

which are substantially free of the diastereomer (4)

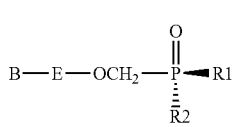

(4)

wherein
R$^1$ is an oxyester which is hydrolyzable in vivo, or hydroxyl;
B is a heterocyclic base;
R$^2$ is hydroxyl, or the residue of an amino acid bonded to the P atom through an amino group of the amino acid and having each carboxy substituent of the amino acid optionally esterified, but not both of R$^1$ and R$^2$ are hydroxyl;

E is —(CH$_2$)$_2$—, —CH(CH$_3$)CH$_2$—, —CH(CH$_2$F)CH$_2$—, —CH(CH$_2$OH)CH$_2$—, —CH(CH=CH$_2$)CH$_2$—, —CH(C≡CH)CH$_2$—, —CH(CH$_2$N$_3$)CH$_2$—,

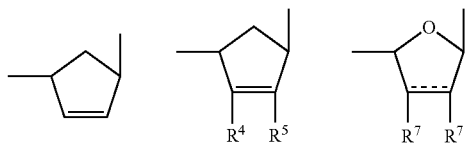

—CH(R$^6$)OCH(R$^{6'}$)—, —CH(R$^9$)CH$_2$O— or —CH(R$^8$)O—, wherein the right hand bond is linked to the heterocyclic base;

the broken line represents an optional double bond;

R$^4$ and R$^5$ are independently hydrogen, hydroxy, halo, amino or a substituent having 1-5 carbon atoms selected from acyloxy, alkyoxy, alkylthio, alkylamino and dialkylamino;

R$^6$ and R$^{6'}$ are independently H, C$_1$-C$_6$ alkyl, C$_1$-C$_6$ hydroxyalkyl, or C$_2$-C$_7$ alkanoyl;

R$^7$ is independently H, C$_1$-C$_6$ alkyl, or are taken together to form —O— or —CH$_2$—;

R$^8$ is H, C$_1$-C$_6$ alkyl, C$_1$-C$_6$ hydroxyalkyl or C$_1$-C$_6$ haloalkyl; and R$^9$ is H, hydroxymethyl or acyloxymethyl;

and their salts, free base, and solvates.

The diastereomers of structure (3) are designated the (5) isomers at the phosphorus chiral center.

Preferred embodiments of this invention are the diastereomerically enriched compounds having the structure (5a)

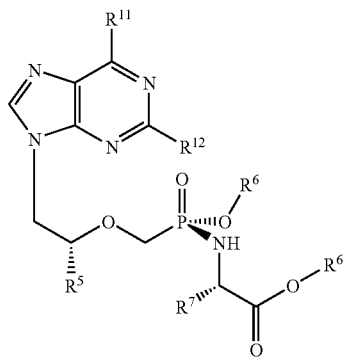

(5a)

which is substantially free of diastereomer (5b)

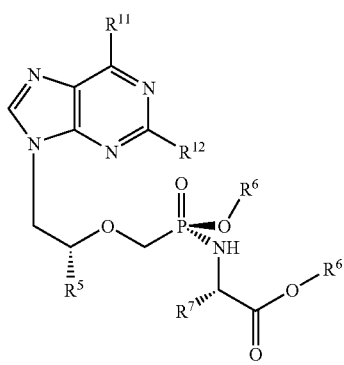

(5b)

wherein

R$^5$ is methyl or hydrogen;

R$^6$ independently is H, alkyl, alkenyl, alkynyl, aryl or arylalkyl, or R$^6$ independently is alkyl, alkenyl, alkynyl, aryl or arylalkyl which is substituted with from 1 to 3 substituents selected from alkylamino, alkylaminoalkyl, dialkylaminoalkyl, dialkylamino, hydroxyl, oxo, halo, amino, alkylthio, alkoxy, alkoxyalkyl, aryloxy, aryloxyalkyl, arylalkoxy, arylalkoxyalkyl, haloalkyl, nitro, nitroalkyl, azido, azidoalkyl, alkylacyl, alkylacylalkyl, carboxyl, or alkylacylamino;

R$^7$ is the side chain of any naturally-occurring or pharmaceutically acceptable amino acid and which, if the side chain comprises carboxyl, the carboxyl group is optionally esterified with an alkyl or aryl group;

R$^{11}$ is amino, alkylamino, oxo, or dialkylamino; and

R$^{12}$ is amino or H;

and its salts, tautomers, free base and solvates.

A preferred embodiment of this invention is the compound of structure (6), 9-[(R)-2-[[(S)-[[(S)-1-(isopropoxycarbonyl)ethyl]amino]phenoxyphosphinyl]methoxy]propyl]adenine, also designated herein GS-7340

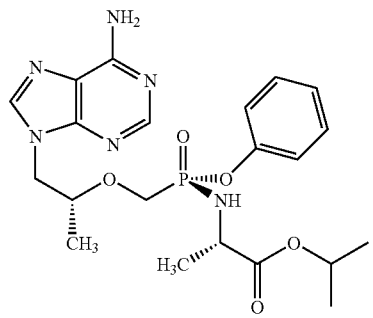

(6)

Another preferred embodiment of this invention is the fumarate salt of structure (5) (structure (7)),9-[(R)-2-[[(S)-[[(S)-1-(isopropoxycarbonyl)ethyl]amino]phenoxyphosphinyl]methoxy]propyl]adenine fumarate (1:1), also designated herein GS-7340-2

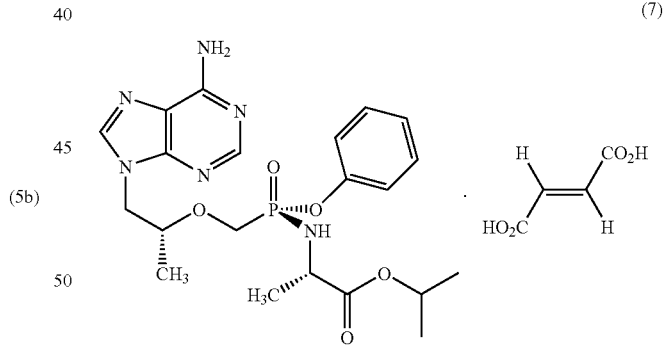

(7)

The compounds of structures (1)-(7) optionally are formulated into compositions containing pharmaceutically acceptable excipients. Such compositions are used in effective doses in the therapy or prophylaxis of viral (particularly HIV or hepadnaviral) infections.

In a further embodiment, a method is provided for the facile manufacture of 9-[2-(phosphonomethoxy)propyl]adenine (hereinafter "PMPA" or 9-[2-(phosphonomethoxy)ethyl]adenine (hereinafter "PMEA") using magnesium alkoxide, which comprises combining 9-(2-hydroxypropyl)adenine or 9-(2-hydroxyethyl)adenine, protected p-toluenesulfonyloxymethylphosphonate and magnesium alkoxide, and recovering PMPA or PMEA, respectively.

BRIEF DESCRIPTION OF THE DRAWINGS

FIG. 1 shows HPLC/C-14 traces of PBMC extracts from human blood incubated for 1 h at 37° C. with TDF, GS-7340 and PMPA.

FIG. 2 shows PMPA and Prodrug concentration in plasma and PBMCs following oral administration of GS 7340-2 to Dogs at 10 mg-eq/kg.

FIG. 3 depicts Tenofovir exposure in PBMCs and plasma upon administration of 10 mg-eq/kg in dogs.

DETAILED DESCRIPTION OF THE INVENTION

The methoxyphosphonate nucleotide analogue parent drugs for use in this screening method are compounds having the structure A-OCH$_2$P(O)(OH)$_2$ wherein A is the residue of a nucleoside analogue. These compounds are known

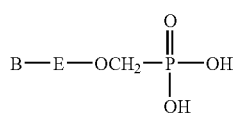

(7a)

per se and are not part of this invention. More particularly, the parent compounds comprise a heterocyclic base B and an aglycon E, in general having the structure wherein the group B is defined below and group E is defined above. Examples are described in U.S. Pat. Nos. 4,659,825, 4,808,716, 4,724,233, 5,142,051, 5,130,427, 5,650,510, 5,663,159, 5,302,585, 5,476,938, 5,696,263, 5,744,600, 5,688,778, 5,386,030, 5,733,896, 5,352,786, and 5,798,340, and EP 821,690 and 654,037.

The prodrugs for use in the screening method of this invention are covalently modified analogues of the parent methoxyphosphonate nucleotide analogues described in the preceding paragraph. In general, the phosphorus atom of the parent drug is the preferred site for prodrug modification, but other sites are found on the heterocyclic base B or the aglycon E. Many such prodrugs are already known. Primarily, they are esters or amidates of the phosphorus atom, but also include substitutions on the base and aglycon. None of these modifications per se is part of this invention and none are to be considered limiting on the scope of the invention herein.

The phosphorus atom of the methoxyphosphonate nucleotide analogues contains two valences for covalent modification such as amidation or esterification (unless one phosphoryl hydroxyl is esterified to an aglycon E hydroxyl substituent, whereupon only one phosphorus valence is free for substitution). The esters typically are aryloxy. The amidates ordinarily are naturally occurring monoamino acids having free carboxyl group(s) esterified with an alkyl or aryl group, usually phenyl, cycloalkyl, or t-, n- or s- alkyl groups. Suitable prodrugs for use in the screening method of this invention are disclosed for example in U.S. Pat. No. 5,798,340. However, any prodrug which is potentially believed to be capable of being converted in vivo within target tissue cells to the free methoxyphosphonate nucleotide analogue parent drug, e.g., whether by hydrolysis, oxidation, or other covalent transformation resulting from exposure to biological tissues, is suitable for use in the method of this invention. Such prodrugs may not be known at this time but are identified in the future and thus become suitable candidates available for testing in the method of this invention. Since the prodrugs are simply candidates for screening in the methods their structures are not relevant to practicing or enabling the screening method, although of course their structures ultimately are dispositive of whether or not a prodrug will be shown to be selective in the assay.

The pro-moieties bound to the parent drug may be the same or different. However, each prodrug to be used in the screening assay will differ structurally from the other prodrugs to be tested. Distinct, i.e. structurally different, prodrugs generally are selected on the basis of either their stereochemistry or their covalent structure, or these features are varied in combination. Each prodrug tested, however, desirably is structurally and stereochemically substantially pure, else the output of the screening assay will be less useful. It is of course within the scope of this invention to test only a single prodrug in an individual embodiment of the method of this invention, although typically then one would compare the results with prior studies with other prodrugs.

We have found that the stereochemistry of the prodrugs is capable of influencing the enrichment in target tissues. Chiral sites are at the phosphorus atom and are also found in its substituents. For example, amino acid used in preparing amidates may be D or L forms, and the phosphonate esters or the amino acid esters can contain chiral centers as well. Chiral sites also are found on the nucleoside analogue portion of the molecules, but these typically are already dictated by the stereochemistry of the parent drug and will not be varied as part of the screen. For example the R isomer of PMPA is preferred as it is more active than the corresponding S isomer. Typically these diasteromers or enantiomers will be chirally enriched if not pure at each site so that the results of the screen will be more meaningful. As noted, distinctiveness of stereoisomers is conferred by enriching or purifying the stereoisomer (typically this will be a diastereomer rather than an enantiomer in the case of most methoxyphosphonate nucleotide analogues) free of other stereoisomers at the chiral center in question, so that each test compound is substantially homogeneous. By substantially homogeneous or chirally enriched, we mean that the desired stereoisomer constitutes greater than about 60% by weight of the compound, ordinarily greater than about 80% and preferably greater than about 95%.

Novel Screening Method

Once at least one candidate prodrug has been selected, the remaining steps of the screening method of this invention are used to identify a prodrug possessing the required selectivity for the target tissue. Most conveniently the prodrugs are labeled with a detectable group, e.g. radiolabeled, in order to facilitate detection later in tissues or cells. However, a label is not required since other suitable assays for the prodrug or its metabolites (including the parent drug) can also be employed. These assays could include mass spectrometry, HPLC, bioassays or immunoassays for instance. The assay may detect the prodrug and any one or more of its metabolites, but preferably the assay is conducted to detect only the generation of the parent drug. This is based on the assumption (which may not be warranted in all cases) that the degree and rate of conversion of prodrug to antivirally active parent diphosphate is the same across all tissues tested. Otherwise, one can test for the diphosphate.

The target tissue preferably will be lymphoid tissue when screening for prodrugs useful in the treatment of HIV infection. Lymphoid tissue will be known to the artisan and includes CD4 cells, lymphocytes, lymph nodes, macrophages and macrophage-like cells including monocytes such as peripheral blood monocytic cells (PBMCs) and glial cells. Lymphoid tissue also includes non-lymphoid tissues that are enriched in lymphoid tissues or cells, e.g. lung, skin and spleen. Other targets for other antiviral drugs of course will be the primary sites of replication or latency for the particular virus concerned, e.g., liver for hepatitis and peripheral nerves for HSV. Similarly, target tissues for tumors will in fact be the tumors themselves. These tissues are all well-known to the artisan and would not require undue experimentation to select. When screening for antiviral compounds, target tissue can be infected by the virus.

Non-target tissues or cells also are screened as part of the method herein. Any number or identity of such tissues or cells can be employed in this regard. In general, tissues for which the parent drug is expected to be toxic will be used as non-target tissues. The selection of a non-target tissue is entirely dependent upon the nature of the prodrug and the activity of the parent. For example, non-hepatic tissues would be selected for prodrugs against hepatitis, and untransformed cells of the same tissue as the tumor will suffice for the antitumor-selective prodrug screen.

It should be noted that the method of this invention is distinct from studies typically undertaken to determine oral bioavailability of prodrugs. In oral bioavailability studies, the objective is to identify a prodrug which passes into the systemic circulation substantially converted to parent drug. In the present invention, the objective is to find prodrugs that are not metabolized in the gastrointestinal tract or circulation. Thus, target tissues to be evaluated in the method of this invention generally do not include the small intestines or, if the intestines are included, then the tissues also include additional tissues other than the small intestines.

The target and non-target tissues used in the screening method of this invention typically will be in an intact living animal. Prodrugs containing esters are more desirably tested in dogs, monkeys or other animals than rodents; mice and rat plasma contains high circulating levels of esterases that may produce a misleading result if the desired therapeutic subject is a human or higher mammal.

It is not necessary to practice this method with intact animals. It also is within the scope of this invention to employ perfused organs, in vitro culture of organs (e.g. skin grafts) or cell lines maintained in various forms of cell culture, e.g. roller bottles or zero gravity suspension systems. For example, MT-2 cells can be used as a target tissue for selecting HIV prodrugs. Thus, the term "tissue" shall not be construed to require organized cellular structures, or the structures of tissues as they may be found in nature, although such would be preferred. Rather, the term "tissue" shall be construed to be synonymous with cells of a particular source, origin or differentiation stage.

The target and non-target tissue may in fact be the same tissue, but the tissues will be in different biological status. For example, the method herein could be used to select for prodrugs that confer activity in virally-infected tissue (target tissue) but which remain substantially inactive in virally-uninfected cells (corresponding non-target tissue). The same strategy would be employed to select prophylactic prodrugs, i.e., prodrugs metabolized to antivirally active forms incidental to viral infection but which remain substantially unmetabolized in uninfected cells. Similarly, prodrugs could be screened in transformed cells and the untransformed counterpart tissue. This would be particularly useful in comparative testing to select prodrugs for the treatment of hematological malignancies, e.g. leukemias.

Without being limited by any particular theory of operation, tissue selective prodrugs are thought to be selectively taken up by target cells and/or selectively metabolized within the cell, as compared to other tissues or cells. The unique advantage of the methoxyphosphonate prodrugs herein is that their metabolism to the dianion at physiological pH ensures that they will be unable to diffuse back out of the cell. They therefore remain effective for lengthy periods of time and are maintained at elevated intracellular concentrations, thereby exhibiting increased potency. The mechanisms for enhanced activity in the target tissue are believed to include enhanced uptake by the target cells, enhanced intracellular retention, or both mechanisms working together. However, the manner in which selectivity or enhanced delivery occurs in the target tissue is not important. It also is not important that all of the metabolic conversion of the prodrug to the parent compound occurs within the target tissue. Only the final drug activity-conferring conversion need occur in the target tissue; metabolism in other tissues may provide intermediates finally converted to antiviral forms in the target tissue.

The degree of selectivity or enhanced delivery that is desired will vary with the parent compound and the manner in which it is measured (% dose distribution or parent drug concentration). In general, if the parent drug already possess a generous therapeutic window, a low degree of selectivity may be sufficient for the desired prodrug. On the other hand, toxic compounds may require more extensive screening to identify selective prodrugs. The relative expense of the method of this invention can be reduced by screening only in the target tissue and tissues against which the parent compound is known to be relatively toxic, e.g. for PMEA, which is nephrotoxic at higher doses, the primary focus will be on kidney and lymphoid tissues.

The step of determining the relative antiviral activity of a prodrug in the selected tissues ordinarily is accomplished by assaying target and non-target tissues for the relative presence or activity of a metabolite of the prodrug, which metabolite is known to have, or is converted to, a metabolite having antiviral or antitumor activity.

Thus, typically one would determine the relative amount of the parent drug in the tissues over substantially the same time course in order to identify prodrugs that are preferentially metabolized in the target tissue to an antivirally or antitumor active metabolite or precursor thereof which in the target tissue ultimately produces the active metabolite. In the case of antiviral compounds, the active metabolite is the diphosphate of the phosphonate parent compounds. It is this metabolite that is incorporated into the viral nucleic acid, thereby truncating the elongating nucleic acid strand and halting viral replication. Metabolites of the prodrug can be anabolic metabolites, catabolic metabolites, or the product of anabolism and catabolism together. The manner in which the metabolite is produced is not important in the practice of the method of this invention.

The method of this invention is not limited to assaying a metabolite which per se possesses antiviral or antitumor activity. Instead, one can assay inactive precursors of the active metabolites. Precursors of the antivirally active diphosphate metabolite include the monophosphate of the parent drug, monophosphates of other metabolites of the parent drug (e.g., an intermediate modification of a substituent on the heterocyclic base), the parent itself and metabolites generated by the cell in converting the prodrug to the parent prior to phosphorylation. The precursor structures may vary considerably as they are the result of cellular metabolism. However, this information is already known or could be readily determined by one skilled in the art.

If the prodrug being assayed does not exhibit antitumor or antiviral activity per se then adjustments to the raw assay results may be required. For example, if the intracellular processing of the inactive metabolite to an active metabolite occurs at different rates among the tissues being tested, the raw assay results with the inactive metabolite would need to be adjusted to take account of the differences among the cell types because the relevant parameter is the generation of activity in the target tissue, not accumulation of inactive metabolites. However, determining the proper adjustments would be within the ordinary skill. Thus, when step (d) of the method herein calls for determining the activity, activity can be either measured directly or extrapolated. It does not mean that the method herein is limited to only assaying intermediates that are active per se. For instance, the absence or decline of the prodrug in the test tissues also could be assayed. Step (d) only requires assessment of the activity conferred by the prodrug as it interacts with the tissue concerned, and this may be based on extrapolation or other indirect measurement.

Step (d) of the method of this invention calls for determining the "relative" activity of the prodrug. It will be understood that this does not require that each and every assay or series of assays necessarily must also contain runs with the selected non-target tissue. On the contrary, it is within the scope of this invention to employ historical controls of the non-target tissue or tissues, or algorithms representing results to be expected from such non-target tissues, in order to provide the benchmark non-target activity.

The results obtained in step (d) are then used optimally to select or identify a prodrug which produces greater antiviral activity in the target tissue than in the non-target tissue. It is this prodrug that is selected for further development.

It will be appreciated that some preassessment of prodrug candidates can be undertaken before the practice of the method of this invention. For example, the prodrug will need to be capable of passing largely unmetabolized through the gastrointestinal tract, it will need to be substantially stable in blood, and it should be able to permeate cells at least to some degree. In most cases it also will need to complete a first pass of the hepatic circulation without substantial metabolism. Such prestudies are optional, and are well-known to those skilled in the art.

The same reasoning as is described above for antiviral activity is applicable to antitumor prodrugs of methoxyphosphonate nucleotide analogues as well. These include, for example, prodrugs of PMEG, the guanyl analogue of PMEA. In this case, cytotoxic phosphonates such as PMEG are worthwhile candidates to pursue as their cytotoxicity in fact confers their antitumor activity.

A compound identified by this novel screening method then can be entered into a traditional preclinical or clinical program to confirm that the desired objectives have been met. Typically, a prodrug is considered to be selective if the activity or concentration of parent drug in the target tissue (% dose distribution) is greater than 2×, and preferably 5×, that of the parent compound in non-target tissue. Alternatively, a prodrug candidate can be compared against a benchmark prodrug. In this case, selectivity is relative rather than absolute. Selective prodrugs will be those resulting in greater than about 10× concentration or activity in the target tissue as compared with the prototype, although the degree of selectivity is a matter of discretion.

Novel Method for Preparation of Starting Materials or Intermediates

Also included herein is an improved method for manufacture of preferred starting materials (parent drugs) of this invention, PMEA and (R)-PMPA. Typically, this method comprises reacting 9-(2-hydroxypropyl)adenine (HPA) or 9-(2-hydroxyethyl)adenine (HEA) with a magnesium alkoxide, thereafter adding the protected aglycon synthon p-toluene-sulfonyloxymethylphosphonate (tosylate) to the reaction mixture, and recovering PMPA or PMEA, respectively.

Preferably, HPA is the enriched or isolated R enantiomer. If a chiral HPA mixture is used, R-PMPA can be isolated from the chiral PMPA mixture after the synthesis is completed.

Typically the tosylate is protected by lower alkyl groups, but other suitable groups will be apparent to the artisan. It may be convenient to employ the tosylate presubstituted with the prodrug phosphonate substituents which are capable of acting as protecting groups in the tosylation reaction, thereby allowing one to bypass the deprotection step and directly recover prodrug or an intermediate therefore.

The alkyl group of the magnesium alkoxide is not critical and can be any $C_1$-$C_6$ branched or normal alkyl, but is preferably t-butyl (for PMPA) or isopropyl (for PMEA). The reaction conditions also are not critical, but preferably comprise heating the reaction mixture at about 70-75° C. with stirring or other moderate agitation.

If there is no interest in retaining the phosphonate substituents, the product is deprotected (usually with bromotrimethylsilane where the tosylate protecting group is alkyl), and the product then recovered by crystallization or other conventional method as will be apparent to the artisan.

Heterocyclic Base

In the compounds of this invention depicted in structures (3) and (4), the heterocyclic base B is selected from the structures

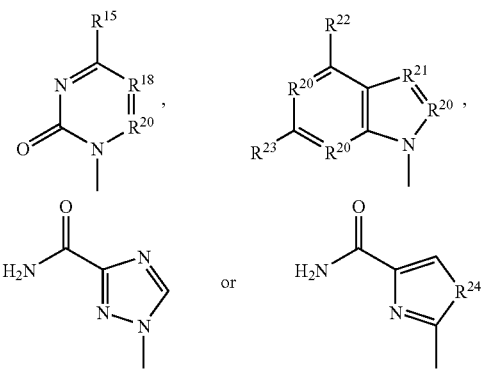

wherein
$R^{15}$ is H, OH, F, Cl, Br, I, $OR^{16}$, SH, $SR^{16}$, $NH_2$, or $NHR^{17}$;
$R^{16}$ is $C_1$-$C_6$ alkyl or $C_2$-$C_6$ alkenyl including —$CH_3$, —$CH_2CH_3$, —$CH_2C\equiv CH$, —$CH_2CH=CH_2$ and —$C_3H_7$;
$R^{17}$ is $C_1$-$C_6$ alkyl or $C_2$-$C_6$ alkenyl including —$CH_3$, —$CH_2CH_3$, —$CH_2C\equiv CH$, —$CH_2CH=CH_2$, and —$C_3H_7$;
$R^{18}$ is N, CF, CCl, CBr, CI, $CR^{19}$, $CSR^{19}$, or $COR^{19}$;
$R^{19}$ is H, $C_1$-$C_9$ alkyl, $C_2$-$C_9$ alkenyl, $C_2$-$C_9$ alkynyl, $C_1$-$C_9$ alkyl-$C_1$-$C_9$ alkoxy, or $C_7$-$C_9$ aryl-alkyl unsubstituted or substituted by OH, F, Cl, Br or I, $R^{19}$ therefore including —$CH_3$, —$CH_2CH_3$, —$CHCH_2$, —$CHCHBr$, —$CH_2CH_2Cl$, —$CH_2CH_2F$, —$CH_2CCH$, —$CH_2CHCH_2$, —$C_3H_7$, —$CH_2OH$, —$CH_2OCH_3$, —$CH_2OC_2H_5$, —$CH_2OCCH$, —$CH_2OCH_2CHCH_2$, —$CH_2C_3H_7$, —$CH_2CH_2OH$, —$CH_2CH_2OCH_3$, —$CH_2CH_2OC_2H_5$, —$CH_2CH_2OCCH$, —$CH_2CH_2OCH_2CHCH_2$, and —$CH_2CH_2OC_3H_7$;
$R^{20}$ is N or CH;
$R^{21}$ is N, CH, CCN, $CCF_3$, $CC\equiv CH$ or $CC(O)NH_2$;
$R^{22}$ is H, OH, $NH_2$, SH, $SCH_3$, $SCH_2CH_3$, $SCH_2C\equiv CH$, $SCH_2CH=CH_2$, $SC_3H_7$, $NH(CH_3)$, $N(CH_3)_2$, $NH(CH_2CH_3)$, $N(CH_2CH_3)_2$, $NH(CH_2C\equiv CH)$, $NH(CH_2CHCH_2)$, $NH(C_3H_7)$, halogen (F, Cl, Br or I) or X wherein X is —$(CH_2)_m(O)_n(CH_2)_mN(R^{10})_2$ wherein each m is independently 0-2, n is 0-1, and
$R^{10}$ independently is H,
$C_1$-$C_{15}$ alkyl, $C_2$-$C_{15}$ alkenyl, $C_6$-$C_{15}$ arylalkenyl, $C_6$-$C_{15}$ arylalkynyl, $C_2$-$C_{15}$ alkynyl, $C_1$-$C_6$-alkylamino-$C_1$-$C_6$ alkyl, $C_5$-$C_{15}$ aralkyl, $C_6$-$C_{15}$ heteroaralkyl, $C_5$-$C_6$ aryl, $C_2$-$C_6$ heterocycloalkyl, $C_2$-$C_{15}$ alkyl, $C_3$-$C_{15}$ alkenyl, $C_6$-$C_{15}$ arylalkenyl, $C_3$-$C_{15}$ alkynyl, $C_7$-$C_{15}$ arylalkynyl, $C_1$-$C_6$-alkylamino-$C_1$-$C_6$ alkyl, $C_5$-$C_{15}$ aralkyl, $C_6$-$C_{15}$ heteroalkyl or $C_3$-$C_6$ heterocycloalkyl wherein methylene in the alkyl moiety not adjacent to $N^6$ has been replaced by —O—, optionally both $R^{10}$ are joined together with N to form a saturated or unsaturated $C_2$-$C_5$ heterocycle containing one or two N heteroatoms and optionally an additional O or S heteroatom, or one of the foregoing $R^{10}$ groups which is substituted with 1 to 3 halo, CN or $N_3$; but optionally at least one $R^{10}$ group is not H;

$R^{23}$ is H, OH, F, Cl, Br, I, $SCH_3$, $SCH_2CH_3$, $SCH_2C\equiv CH$, $SCH_2CHCH_2$, $SC_3H_7$, $OR^{16}$, $NH_2$, $NHR^{17}$ or $R_{22}$; and $R^{24}$ is O, S or Se.

B also includes both protected and unprotected heterocyclic bases, particularly purine and pyrimidine bases. Protecting groups for exocyclic amines and other labile groups are known (Greene et al. "Protective Groups in Organic Synthesis") and include N-benzoyl, isobutyryl, 4,4'-dimethoxytrityl (DMT) and the like. The selection of protecting group will be apparent to the ordinary artisan and will depend upon the nature of the labile group and the chemistry which the protecting group is expected to encounter, e.g. acidic, basic, oxidative, reductive or other conditions. Exemplary protected species are $N^4$-benzoylcytosine, $N^6$-benzoyladenine, $N^2$-isobutyrylguanine and the like.

Protected bases have the formulas Xa.1, XIa.1, XIb.1, XIIa.1 or XIIIa.1

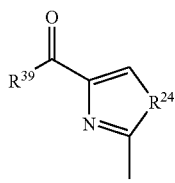
(Xa.1)

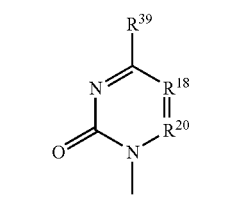
(XIa.1)

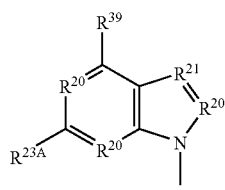
(XIb.1)

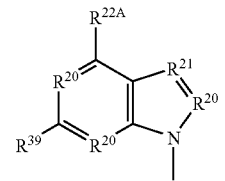
(XIIa.1)

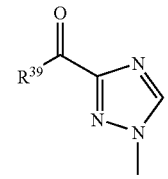
(XIIIa.1)

wherein $R^{18}$, $R^{20}$, $R^{21}$, $R^{24}$ have the meanings previously defined; $R^{22A}$ is $R^{39}$ or $R^{22}$ provided that $R^{22}$ is not $NH_2$; $R^{23A}$ is $R^{39}$ or $R^{23}$ provided that $R^{23}$ is not $NH_2$; $R^{39}$ is $NHR^{40}$, $NHC(O)R^{36}$ or $CR^{41}N(R^{38})_2$ wherein $R^{36}$ is $C_1$-$C_{19}$ alkyl, $C_1$-$C_{19}$ alkenyl, $C_3$-$C_{10}$ aryl, adamantoyl, alkylanyl, or $C_3$-$C_{10}$ aryl substituted with 1 or 2 atoms or groups selected from halogen, methyl, ethyl, methoxy, ethoxy, hydroxy and cyano; $R^{38}$ is $C_1$-$C_{10}$ alkyl, or both $R^{38}$ together are 1-morpholino, 1-piperidine or 1-pyrrolidine; $R^{40}$ is $C_1$-$C_{1a}$ alkyl, including methyl, ethyl, propyl, isopropyl, butyl, isobutyl, t-butyl, pentyl, hexyl, octyl and decanyl; and $R^{41}$ is hydrogen or $CH_3$.

For bases of structures XIa.1 and XIb.1, if $R^{39}$ is present at $R^{22A}$ or $R^{23A}$, both $R^{39}$ groups on the same base will generally be the same. Exemplary $R^{36}$ are phenyl, phenyl substituted with one of the foregoing $R^{36}$ aryl substituents, —$C_{10}H_{15}$ (where $C_{10}H_{15}$ is 2-adamantoyl), —$CH_2$—$C_6H_5$, —$C_6H_5$, —$CH(CH_3)_2$, —$CH_2CH_3$, methyl, butyl, t-butyl, heptanyl, nonanyl, undecanyl, or undecenyl.

Specific bases include hypoxanthine, guanine, adenine, cytosine, inosine, thymine, uracil, xanthine, 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 1-deaza derivatives of 2-aminopurine, 2,6-diaminopurine, 2-amino-6-chloropurine, hypoxanthine, inosine and xanthine; 7-deaza derivatives of 2-aminopurine, 2,6-diaminopurine, 2-amino-6-chloropurine, hypoxanthine, inosine and xanthine; 3-deaza derivatives of 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil and 5-propynyluracil.

Preferably, B is a 9-purinyl residue selected from guanyl, 3-deazaguanyl, 1-deazaguanyl, 8-azaguanyl, 7-deazaguanyl, adenyl, 3-deazaadenyl, 1-dezazadenyl, 8-azaadenyl, 7-deazaadenyl, 2,6-diaminopurinyl, 2-aminopurinyl, 6-chloro-2-aminopurinyl and 6-thio-2-aminopurinyl, or a B' is a 1-pyrimidinyl residue selected from cytosinyl, 5-halocytosinyl, and 5-($C_1$-$C_3$-alkyl)cytosinyl.

Preferred B groups have the formula

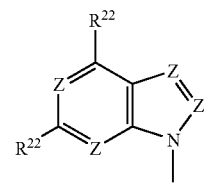

wherein $R^{22}$ independently is halo, oxygen, $NH_2$, X or H, but optionally at least one $R^{22}$ is X;

X is —$(CH_2)_m(O)_n(CH_2)_mN(R^{10})_2$ wherein m is 0-2, n is 0-1, and $R^{10}$ independently is H, $C_1$-$C_{15}$ alkyl, $C_2$-$C_{15}$ alkenyl, $C_6$-$C_{15}$ arylalkenyl, $C_6$-$C_1$ arylalkynyl, $C_2$-$C_{15}$ alkynyl, $C_1$-$C_6$-alkylamino-$C_1$-$C_6$ alkyl, $C_5$-$C_{15}$ aralkyl, $C_6$-$C_{15}$ heteroaralkyl, $C_5$-$C_6$ aryl, $C_2$-$C_6$ heterocycloalkyl, $C_2$-$C_{15}$ alkyl, $C_3$-$C_{15}$ alkenyl, $C_6$-$C_{15}$ arylalkenyl, $C_3$-$C_{15}$ alkynyl, $C_7$-$C_{15}$ arylalkynyl, $C_1$-$C_6$-alkylamino-$C_1$-$C_6$ alkyl, $C_5$-$C_{15}$ aralkyl, $C_6$-$C_{15}$ heteroalkyl or $C_3$-$C_6$ heterocycloalkyl wherein methylene in the alkyl moiety not adjacent to $N^6$ has been replaced by —O—, optionally both $R^{10}$ are joined together with N to form a saturated or unsaturated $C_2$-$C_5$ heterocycle containing one or two N heteroatoms and optionally an additional O or S heteroatom, or one of the foregoing $R^{10}$ groups is substituted with 1 to 3 halo, CN or $N_3$; but optionally at least one $R^{10}$ group is not H; and Z is N or CH, provided that the heterocyclic nucleus varies from purine by no more than one Z.

E groups represent the aglycons employed in the methoxyphosphonate nucleotide analogues. Preferably, the E group is —$CH(CH_3)CH_2$— or —$CH_2CH_2$—. Also, it is preferred that the side groups at chiral centers in the aglycon be substantially solely in the (R) configuration (except for hydroxymethyl, which is the enriched (S) enantiomer).

$R^1$ is an in vivo hydrolyzable oxyester having the structure —$OR^{35}$ or —$OR^6$ wherein $R^{35}$ is defined in column 64, line 49 of U.S. Pat. No. 5,798,340, herein incorporated by reference, and $R^6$ is defined above. Preferably $R^1$ is aryloxy, ordinarily unsubstituted or para-substituted (as defined in $R^6$) phenoxy.

$R^2$ is an amino acid residue, optionally provided that any carboxy group linked by less than about 5 atoms to the amidate N is esterified. $R^2$ typically has the structure

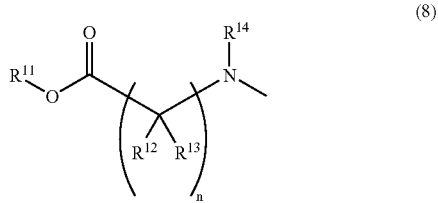

(8)

wherein n is 1 or 2;

$R^{11}$ is $R^6$ or H; preferably $R^6$=$C_3$-$C_9$ alkyl; $C_3$-$C_9$ alkyl substituted independently with OH, halogen, O or N; $C_3$-$C_6$ aryl; $C_3$-$C_6$ aryl which is independently substituted with OH, halogen, O or N; or $C_3$-$C_6$ arylalkyl which is independently substituted with OH, halogen, O or N;

$R^{12}$ independently is H or $C_1$-$C_9$ alkyl which is unsubstituted or substituted by substituents independently selected from the group consisting of OH, O, N, $COOR^{11}$ and halogen; $C_3$-$C_6$ aryl which is unsubstituted or substituted by substituents independently selected from the group consisting of OH, O, N, $COOR^{11}$ and halogen; or $C_3$-$C_9$ aryl-alkyl which is unsubstituted or substituted by substituents independently selected from the group consisting of OH, O, N, $COOR^{11}$ and halogen;

$R^{13}$ independently is C(O)—$OR^{11}$; amino; amide; guanidinyl; imidazolyl; indolyl; sulfoxide; phosphoryl; $C_1$-$C_3$ alkylamino; $C_1$-$C_3$ alkyldiamino; $C_1$-$C_6$ alkenylamino; hydroxy; thiol; $C_1$-$C_3$ alkoxy; $C_1$-$C_3$ alkthiol; $(CH_2)_nCOOR^{11}$; $C_1$-$C_6$ alkyl which is unsubstituted or substituted with OH, halogen, SH, $NH_2$, phenyl, hydroxyphenyl or $C_7$-$C_{10}$ alkoxyphenyl;

$C_2$-$C_6$ alkenyl which is unsubstituted or substituted with OH, halogen, SH, $NH_2$, phenyl, hydroxyphenyl or $C_7$-$C_{10}$ alkoxyphenyl; and $C_6$-$C_{12}$ aryl which is unsubstituted or substituted with OH, halogen, SH, $NH_2$, phenyl, hydroxyphenyl or $C_7$-$C_{10}$ alkoxyphenyl; and $R^{14}$ is H or $C_1$-$C_9$ alkyl or $C_1$-$C_9$ alkyl independently substituted with OH, halogen, $COOR^{11}$, O or N; $C_3$-$C_6$ aryl; $C_3$-$C_6$ aryl which is independently substituted with OH, halogen, $COOR^{11}$, O or N; or $C_3$-$C_6$ arylalkyl which is independently substituted with OH, halogen, $COOR^{11}$, O or N.

Preferably, $R^{11}$ is $C_1$-$C_6$ alkyl, most preferably isopropyl, $R^{13}$ is the side chain of a naturally occurring amino acid, n=1, $R^{12}$ is H and $R^{14}$ is H. In the compound of structure (2), the invention includes metabolites in which the phenoxy and isopropyl esters have been hydrolyzed to —OH. Similarly, the de-esterified enriched phosphonoamidate metabolites of compounds (5a), 5(b) and (6) are included within the scope of this invention.

Aryl and "O" or "N" substitution are defined in column 16, lines 42-58, of U.S. Pat. No. 5,798,340.

Typically, the amino acids are in the natural or l amino acids. Suitable specific examples are set forth in U.S. Pat. No. 5,798,340, for instance Table 4 and col. 8-10 therein.

Alkyl as used herein, unless stated to the contrary, is a normal, secondary, tertiary or cyclic hydrocarbon. Unless stated to the contrary alkyl is $C_1$-$C_{12}$. Examples are —$CH_3$, —$CH_2CH_3$, —$CH_2CH_2CH_3$, —$CH(CH_3)_2$, —$CH_2CH_2CH_2CH_3$), —$CH_2CH(CH_3)_2$, —$CH(CH_3)$ $CH_2CH_3$, —$C(CH_3)_3$, —$CH_2CH_2CH_2CH_2CH_3$, —$CH(CH_3)$ $CH_2CH_2CH_3$, —$CH(CH_2CH_3)_2$, —$C(CH_3)_2CH_2CH_3$), —$CH(CH_3)CH(CH_3)_2$, —$CH_2CH_2CH(CH_3)_2$, —$CH_2CH$ $(CH_3)CH_2CH_3$, —$CH_2CH_2CH_2CH_2CH_3$, —$CH(CH_3)$ $CH_2CH_2CH_2CH_3$, —$CH(CH_2CH_3)(CH_2CH_2CH_3)$, —$C(CH_3)_2CH_2CH_2CH_3$, —$CH(CH_3)CH(CH_3)CH_2CH_3$, —$CH(CH_3)CH_2CH(CH_3)_2$, —$C(CH_3)(CH_2CH_3)_2$, —$CH$ $(CH_2CH_3)CH(CH_3)_2$, —$C(CH_3)_2CH(CH_3)_2$, and —$CH$ $(CH_3)C(CH_3)_3$. Alkenyl and alkynyl are defined in the same fashion, but contain at least one double or triple bond, respectively.

Where enol or keto groups are disclosed, the corresponding tautomers are to be construed as taught as well.

The prodrug compounds of this invention are provided in the form of free base or the various salts enumerated in U.S. Pat. No. 5,798,340, and are formulated with pharmaceutically acceptable excipients or solvating diluents for use as pharmaceutical products also as set forth in U.S. Pat. No. 5,798,340. These prodrugs have the antiviral and utilities already established for the parent drugs (see U.S. Pat. No. 5,798,340 and other citations relating to the methoxyphosphonate nucleotide analogues). It will be understood that the diastereomer of structure (4) at least is useful as an intermediate in the chemical production of the parent drug by hydrolysis in vitro, regardless of its relatively unselective character as revealed in the studies herein.

The invention will be more fully understood by reference to the following examples:

EXAMPLE 1a

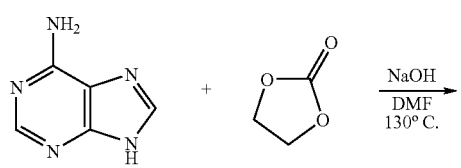

EXAMPLE 1b

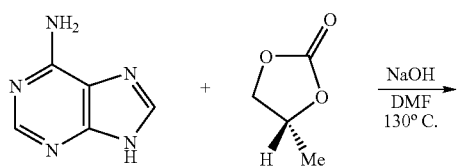

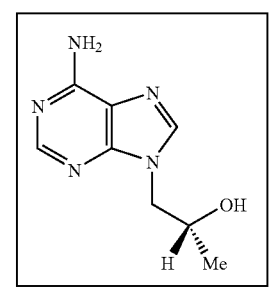

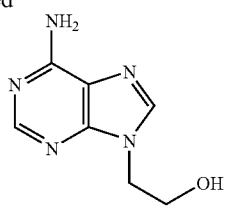

Adenine to PMEA using Magnesium Isopropoxide. To a suspension of adenine (16.8 g, 0.124 mol) in DMF (41.9 ml) was added ethylene carbonate (12.1 g, 0.137 mol) and sodium hydroxide (.100 g, 0.0025 mol). The mixture was heated at 130° C. overnight. The reaction was cooled to below 50° C. and toluene (62.1 ml) was added. The slurry was further cooled to 5° C. for 2 hours, filtered, and rinsed with toluene (2×). The wet solid was dried in vacuo at 65° C. to yield 20.0 g (90%) of 9-(2-hydroxyethyl)adenine as an off-white solid. Mp: 238-240° C.

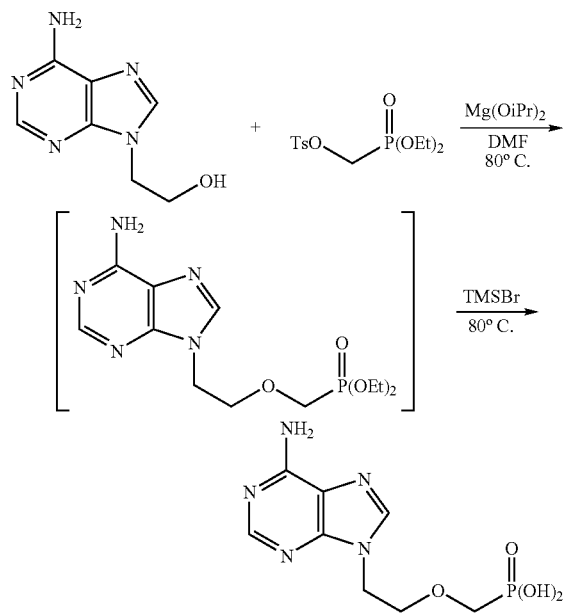

Adenine to PMPA using Magnesium t-Butoxide. To a suspension of adenine (40 g, 0.296 mol) in DMF (41.9 ml) was added (R)-propylene carbonate (34.5 g, 0.338 mol) and sodium hydroxide (0.480 g, 0.012 mol). The mixture was heated at 130° C. overnight. The reaction was cooled to 100° C. and toluene (138 ml) was added followed by methanesulfonic acid (4.7 g, 0.049 mol) while maintaining the reaction temperature between 100-110° C. Additional toluene (114 ml) was added to create a homogeneous solution. The solution was cooled to 3° C. over 7 hours and then held at 3° C. for one hour. The resulting solid was isolated by filtration and rinsed with acetone (2×). The wet solid was dried in vacuo at 80° C. to yield 42.6 g (75%) of (R)-9-[2-(hydroxy)propyl]adenine (HPA) as an off-white solid. Mp: 188-190° C.

9-(2-Hydroxyethyl)adenine (HEA) (20.0 g, 0.112 mol) was suspended in DMF (125 ml) and heated to 80° C. Magnesium isopropoxide (11.2 g, 0.0784 mol), or alternatively magnesium t-butoxide, was added to the mixture followed by diethyl p-toluenesulfonyloxymethylphosphonate (66.0 g, 0.162 mol) over one hour. The mixture was stirred at 80° C. for 7 hours. 30 ml of volatiles were removed via vacuum distillation and the reaction was recharged with 30 ml of fresh DMF. After cooling to room temperature, bromotrimethylsilane (69.6 g, 0.450 mol) was added and the mixture heated to 80° C. for 6 hours. The reaction was concentrated to yield a thick gum. The gum was dissolved into 360 ml water, extracted with 120 ml dichloromethane, adjusted to pH 3.2 with sodium hydroxide, and the resulting slurry stirred at room temperature overnight. The slurry was cooled to 4° C. for one hour. The solids were isolated by filtration, washed with water (2×), and dried in vacuo at 56° C. to yield 20 g (65.4%) of 9-[2-(phosphonomethoxy)ethyl]adenine (PMEA) as a white solid. Mp:>200° C. dec. $^1$H NMR (D$_2$O) δ 3.49 (t, 2H); 3.94 (t, 2H); 4.39 (t, 2H); 8.13 (s, 1H); 8.22 (s, 1H).

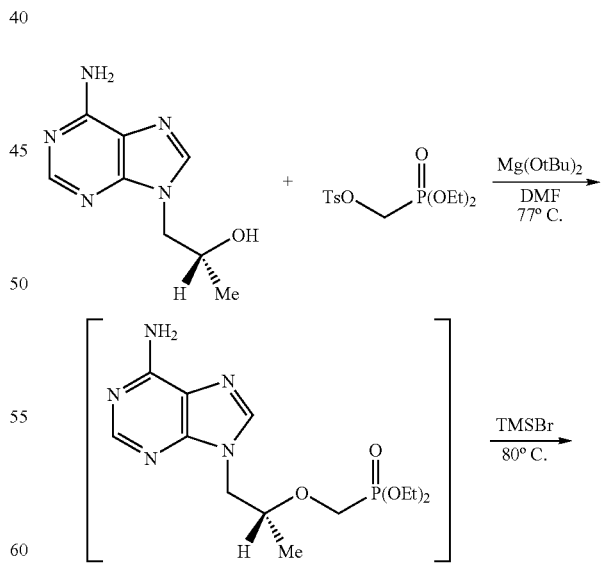

-continued

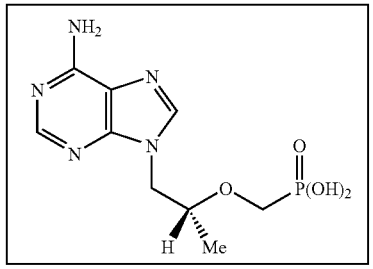

(R)-9-[2-(hydroxy)propyl]adenine (HPA) (20.0 g, 0.104 mol) was suspended in DMF (44.5 ml) and heated to 65° C. Magnesium t-butoxide (14.2 g, 0.083 mol), or alternatively magnesium isopropoxide, was added to the mixture over one hour followed by diethyl p-toluenesulfonyloxymethylphosphonate (66.0 g, 0.205 mol) over two hours while the temperature was kept at 78° C. The mixture was stirred at 75° C. for 4 hours. After cooling to below 50° C., bromotrimethylsilane (73.9 g, 0.478 mol) was added and the mixture heated to 77° C. for 3 hours. When complete, the reaction was heated to 80° C. and volatiles were removed via atmospheric distillation. The residue was dissolved into water (120 ml) at 50° C. and then extracted with ethyl acetate (101 ml). The pH of the aqueous phase was adjusted to pH 1.1 with sodium hydroxide, seeded with authentic (R)-PMPA, and the pH of the aqueous layer was readjusted to pH 2.1 with sodium hydroxide. The resulting slurry was stirred at room temperature overnight. The slurry was cooled to 4° C. for three hours. The solid was isolated by filtration, washed with water (60 ml), and dried in vacuo at 50° C. to yield 18.9 g (63.5%) of crude(R)-9-[2-(phosphonomethoxy)propyl]adenine (PMPA) as an off-white solid.

The crude(R)-9-[2-(phosphonomethoxy)propyl]adenine was heated at reflux in water (255 ml) until all solids dissolved. The solution was cooled to room temperature over 4 hours. The resulting slurry was cooled at 4° C. for three hours. The solid was isolated by filtration, washed with water (56 ml) and acetone (56 ml), and dried in vacuo at 50° C. to yield 15.0 g (50.4%) of (R)-9-[2-(phosphonomethoxy)propyl]adenine (PMPA) as a white solid. Mp: 278-280° C.

EXAMPLE 2

Preparation of GS-7171 (III)

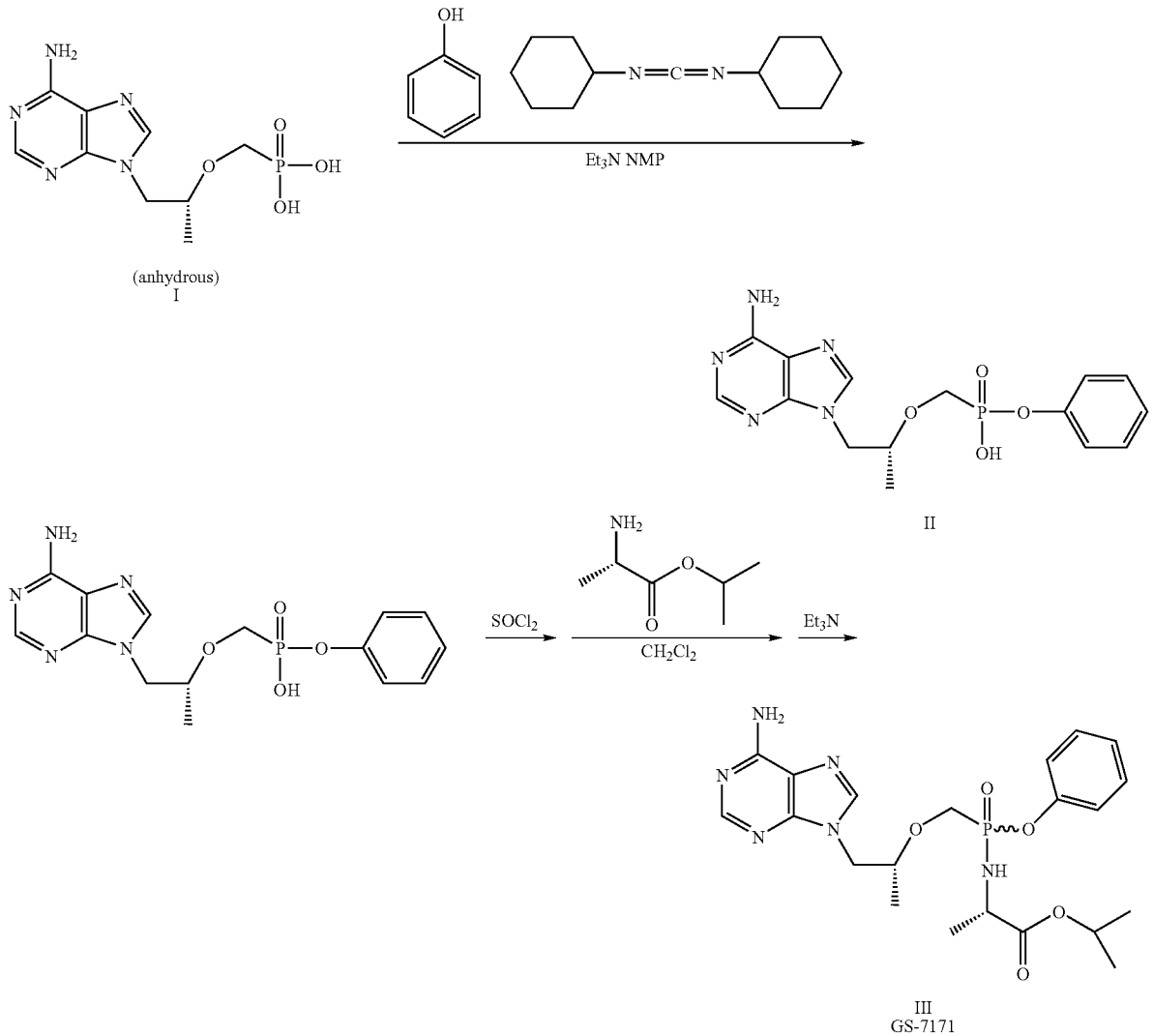

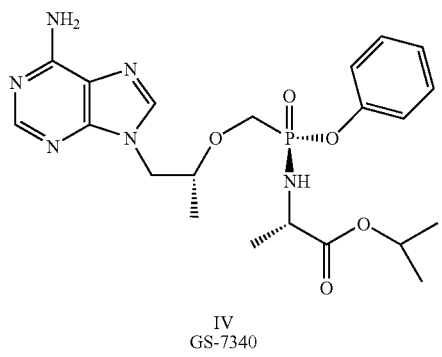

IV
GS-7340

-continued

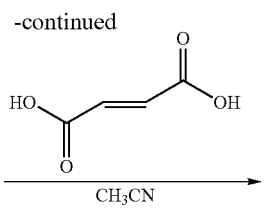

$\xrightarrow{CH_3CN}$

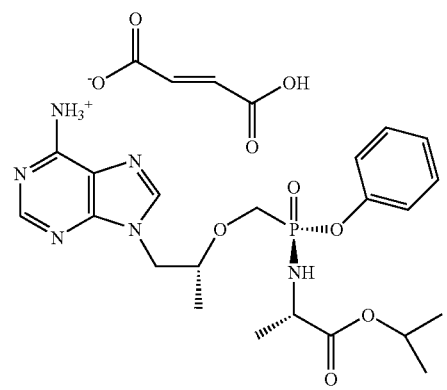

V
GS-7340-02

A glass-lined reactor was charged with anhydrous PMPA, (I) (14.6 kg, 50.8 mol), phenol (9.6 kg, 102 mol), and 1-methyl-2-pyrrolidinone (39 kg). The mixture was heated to 85° C. and triethylamine (6.3 kg, 62.3 mol) added. A solution of 1,3-dicyclohexylcarbodiimide (17.1 kg, 82.9 mol) in 1-methyl-2-pyrrolidinone (1.6 kg) was then added over 6 hours at 100° C. Heating was continued for 16 hours. The reaction was cooled to 45° C., water (29 kg) added, and cooled to 25° C. Solids were removed from the reaction by filtration and rinsed with water (15.3 kg). The combined filtrate and rinse was concentrated to a tan slurry under reduced pressure, water (24.6 kg) added, and adjusted to pH=11 with NaOH (25% in water). Fines were removed by filtration through diatomaceous earth (2 kg) followed by a water (4.4 kg) rinse. The combined filtrate and rinse was extracted with ethyl acetate (28 kg). The aqueous solution was adjusted to pH=3.1 with HCl (37% in water) (4 kg). Crude II was isolated by filtration and washed with methanol (12.7 kg). The crude II wet cake was slurried in methanol (58 kg). Solids were isolated by filtration, washed with methanol (8.5 kg), and dried under reduced pressure to yield 9.33 kg II as a white powder: $^1$H NMR (D$_2$O) δ 1.2 (d, 3H), 3.45 (q, 2H), 3.7 (q, 2H), 4 (m, 2H), 4.2 (q, 2H) 4.35 (dd, 2H), 6.6 (d, 2H), 7 (t, 1H), 7.15 (t, 2H), 8.15 (s, 1H), 8.2 (s, 1H); $^{31}$P NMR (D$_2$O) δ 15.0 (decoupled).

GS-7171 (III). (Scheme 1) A glass-lined reactor was charged with monophenyl PMPA, (II), (9.12 kg, 25.1 mol) and acetonitrile (30.7 kg). Thionyl chloride (6.57 kg, 56.7 mol) was added below 50° C. The mixture was heated at 75° C. until solids dissolved. Reaction temperature was increased to 80° C. and volatiles (11.4 kg) collected by atmospheric distillation under nitrogen. The pot residue was cooled to 25° C., dichloromethane (41 kg) added, and cooled to −29° C. A solution of (L)-alanine isopropyl ester (7.1 kg, 54.4 mol) in dichloromethane (36 kg) was added over 60 minutes at −18° C. followed by triethylamine (7.66 kg, 75.7 mol) over 30 minutes at −18 to −11° C. The reaction mixture was warmed to room temperature and washed five times with sodium dihydrogenphosphate solution (10% in water, 15.7 kg each wash). The organic solution was dried with anhydrous sodium sulfate (18.2 kg), filtered, rinsed with dichloromethane (28 kg), and concentrated to an oil under reduced pressure. Acetone (20 kg) was charged to the oil and the mixture concentrated under reduced pressure. Acetone (18.8 kg) was charged to the resulting oil. Half the product solution was purified by chromatography over a 38×38 cm bed of 22 kg silica gel 60, 230 to 400 mesh. The column was eluted with 480 kg acetone. The purification was repeated on the second half of the oil using fresh silica gel and acetone. Clean product bearing fractions were concentrated under reduced pressure to an oil. Acetonitrile (19.6 kg) was charged to the oil and the mixture concentrated under reduced pressure. Acetonitrile (66.4 kg) was charged and the solution chilled to 0 to −5° C. for 16 hours. Solids were removed by filtration and the filtrate concentrated under reduced pressure to 5.6 kg III as a dark oil: $^1$H NMR (CDCl$_3$) δ 1.1 (m 12H), 3.7 (m, 1H), 4.0 (m, 5H), 4.2 (m, 1H), 5.0 (m, 1H), 6.2 (s, 2H), 7.05 (m, 5H), 8.0 (s, 1H), 8.25 (d, 1H); $^{31}$P NMR (CDCl$_3$) δ 21.0, 22.5 (decoupled).

Alternate Method for GS-7171(III)

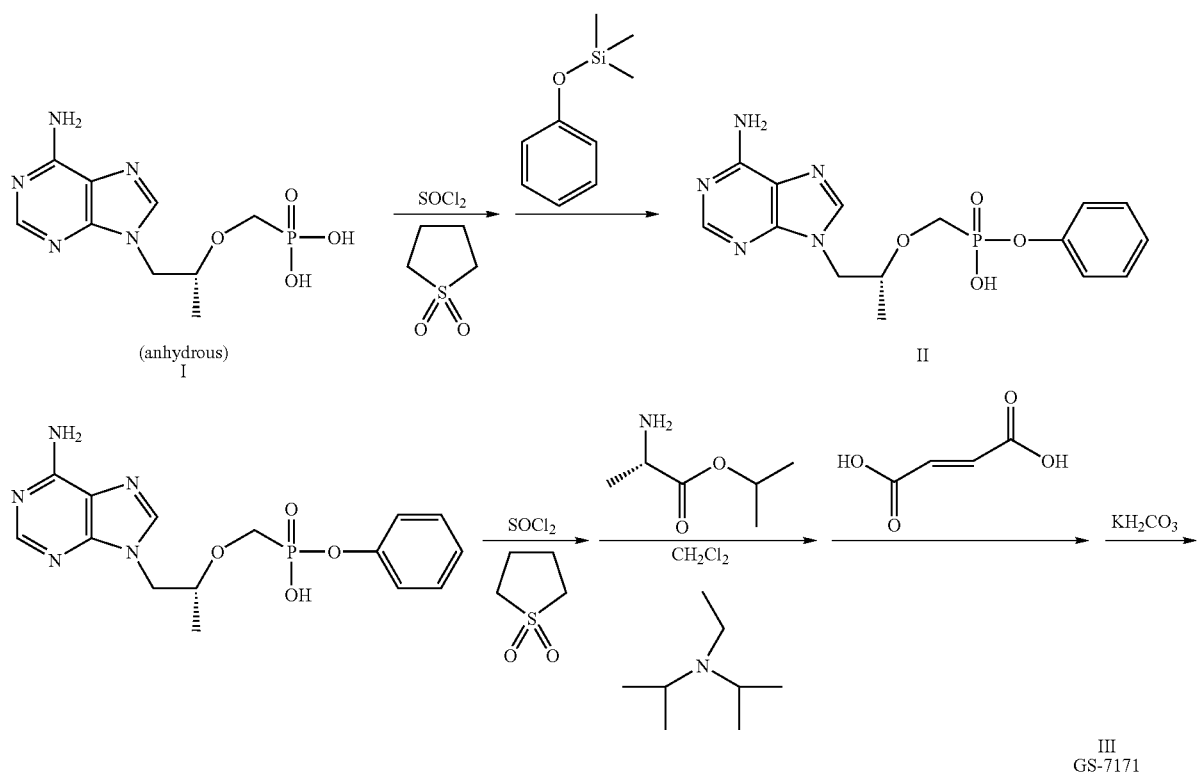

Monophenyl PMPA (II). A round-bottom flask with reflux condenser and nitrogen inlet was placed in a 70° C. oil bath. The flask was charged with anhydrous PMPA (I) (19.2 g, 67 mmol), N,N-dimethylformamide (0.29 g, 3.3 mmol), and tetramethylene sulfone (40 mL). Thionyl chloride (14.2 g, 119 mmol) was added over 4 hours. Heating was increased to 100° C. over the same time. A homogeneous solution resulted. Phenoxytrimethylsilane (11.7 g, 70 mmol) was added to the solution over 5 minutes. Heating in the 100° C. oil bath continued for two hours more. The reaction was poured into rapidly stirring acetone (400 mL) with cooling at 0° C. Solids were isolated by filtration, dried under reduced pressure, and dissolved in methanol (75 mL). The solution pH was adjusted to 3.0 with potassium hydroxide solution (45% aq.) with cooling in ice/water. The resulting solids were isolated by filtration, rinsed with methanol, and dried under reduced pressure to 20.4 g II (Scheme 2) as a white powder.

GS-7171 (III). Monophenyl PMPA (II) (3 g, 8.3 mmol), tetramethylene sulfone (5 mL), and N,N-dimethylformamide (1 drop) were combined in a round bottom flask in a 40° C. oil bath. Thionyl chloride (1.96 g, 16.5 mmol) was added. After 20 minutes the clear solution was removed from heat, diluted with dichloromethane (10 ml), and added to a solution of (L)-alanine isopropyl ester (5 g, 33 mmol) and diisopropylethylamine (5.33 g, 41 mmol) in dichloromethane (20 mL) at −10° C. The reaction mixture was warmed to room temperature and washed three times with sodium dihydrogenphosphate solution (10% aq., 10 mL each wash). The organic solution was dried over anhydrous sodium sulfate and concentrated under reduced pressure to a oil. The oil was combined with fumaric acid (0.77 g, 6.6 mmol) and acetonitrile (40 mL) and heated to reflux to give a homogeneous solution. The solution was cooled in an ice bath and solids isolated by filtration. The solid GS-7171 fumarate salt was dried under reduced pressure to 3.7 g. The salt (3.16 g, 5.3 mmol) was suspended in dichloromethane (30 mL) and stirred with potassium carbonate solution (5 mL, 2.5 M in water) until the solid dissolved. The organic layer was isolated, then washed with water (5 mL), dried over anhydrous sodium sulfate, and concentrated under reduced pressure to afford 2.4 g III as a tan foam.

EXAMPLE 3

Diastereomer Separation by Batch Elution Chromatography

The diastereomers of GS-7171 (III) were resolved by batch elution chromatography using a commercially available Chiralpak AS, 20 μm, 21×250 mm semi-preparative HPLC column with a Chiralpak AS, 20 μm, 21×50 mm guard column. Chiralpak® AS is a proprietary packing material manufactured by Diacel and sold in North America by Chiral Technologies, Inc. (U.S. Pat. Nos. 5,202,433, RE 35,919, 5,434,298, 5,434,299 and 5,498,752). Chiralpak AS is a chiral stationary phase (CSP) comprised of amylosetris[(S)-α-methylbenzyl carbamate] coated onto a silica gel support.

The GS-7171 diastereomeric mixture was dissolved in mobile phase, and approximately 1 g aliquots of GS-7171 were pumped onto the chromatographic system. The undesired diastereomer, designated GS-7339, was the first major broad (approx. 15 min. duration) peak to elute from the column. When the GS-7339 peak had finished eluting, the mobile phase was immediately switched to 100% methyl alcohol, which caused the desired diastereomer, designated GS-7340 (IV), to elute as a sharp peak from the column with the methyl alcohol solvent front. The methyl alcohol was used to reduce the over-all cycle time. After the first couple of injections, both diastereomers were collected as a single large fractions containing one of the purified diastereomers (>99.0% single diastereomer). The mobile phase solvents were removed in vacuo to yield the purified diastereomer as a friable foam.

About 95% of the starting GS-7171 mass was recovered in the two diastereomer fractions. The GS-7340 fraction comprised about 50% of the total recovered mass.

The chromatographic conditions were as follows:
Mobile Phase (Initial): GS-7171-Acetonitrile: Isopropyl Alcohol (90:10)
(Final): 100% Methyl Alcohol
Flow: 10 mL/minute
Run Time: About 45 minute
Detection: UV at 275 nm
Temperature: Ambient
Elution Profile: GS-7339 (diastereomer B)
:GS-7340 (diastereomer A; (IV))

Diastereomer Separation of GS-7171 by SMB Chromatography

For a general description of simulated moving bed (SMB) chromatography, see Strube et al., "Organic Process Research and Development" 2:305-319 (1998).

GS-7340 (IV). GS-7171 (III), 2.8 kg, was purified by simulated moving bed chromatography over 10 cm by 5 cm beds of packing (Chiral Technologies Inc., 20 micron Chiralpak AS coated on silica gel) (1.2 kg). The columns were eluted with 30% methanol in acetonitrile. Product bearing fractions were concentrated to a solution of IV in acetonitrile (2.48 kg). The solution solidified to a crystalline mass wet with acetonitrile on standing. The crystalline mass was dried under reduced pressure to a tan crystalline powder, 1.301 kg IV, 98.7% diastereomeric purity: mp 117-120° C.; $^1$H NMR (CDCl$_3$) δ 1.15 (m 12H), 3.7 (t, 1H), 4.0 (m, 5H), 4.2 (dd, 1H), 5.0 (m, 1H), 6.05 (s, 2H), 7.1 (m, 5H), 8.0 (s, 1H), 8.2 (s, 1H); $^{31}$P NMR (CDCl$_3$) δ 21.0 (decoupled).

Diastereomer Separation by C18 RP-HPLC

GS-7171 (III) was chromatographed by reverse phase HPLC to separate the diastereomers using the following summary protocol.
Chromatographic column: Phenomenex Luna™ C18(2), 5 μm, 100 Å pore size, (Phenomenex, Torrance, Calif.), or equivalent
Guard column: Pellicular C18 (Alltech, Deerfield, Ill.), or equivalent
Mobile Phase: A—0.02% (85%) H$_3$PO$_4$ in water: acetonitrile (95:5)
B—0.02% (85%) H$_3$PO$_4$ in water: acetonitrile (50:50)
Mobile Phase Gradient:

| Time | % Mobile Phase A | % Mobile Phase B |
|---|---|---|
| 0 | 100 | 0 |
| 5 | 100 | 0 |
| 7 | 70 | 30 |
| 32 | 70 | 30 |
| 40 | 0 | 100 |
| 50 | 0 | 100 |

Run Time: 50 minutes
Equilibration Delay: 10 min at 100% mobile phase A
Flow Rate: 1.2 mL/min
Temperature: Ambient
Detection: UV at 260 nm
Sample Solution: 20 mM sodium phosphate buffer, pH 6
Retention Times: GS-7339, about 25 minutes
GS-7340, about 27 minutes Diastereomer Separation by Crystallization GS-7340 (IV). A solution of GS-7171 (III) in acetonitrile was concentrated to an amber foam (14.9 g) under reduced pressure. The foam was dissolved in acetonitrile (20 mL) and seeded with a crystal of IV. The mixture was stirred overnight, cooled to 5° C., and solids isolated by filtration. The solids were dried to 2.3 g IV as white crystals, 98% diastereomeric purity ($^{31}$P NMR): $^1$H NMR (CDCl$_3$) δ 1.15 (m 12H), 3.7 (t, 1H), 3.95 (m, 2H), 4.05 (m, 2H), 4.2 (m, 2H), 5.0 (m, 1H), 6.4 (s, 2H), 7.1 (m, 5H), 8.0 (s, 1H), 8.2 (s, 1H); $^{31}$P NMR (CDCl$_3$) δ 19.5 (decoupled). X-ray crystal analysis of a single crystal selected from this product yielded the following data:

| | |
|---|---|
| Crystal Color, Habit | colorless, column |
| Crystal Dimensions | 0.25 × 0.12 × 0.08 mm |
| Crystal System | orthorhombic |
| Lattice Type | Primitive |
| Lattice Parameters | a = 8.352(1) Å |
| | b = 15.574(2) Å |
| | c = 18.253(2) Å |
| | V = 2374.2(5) Å$^3$ |
| Space Group | P2$_1$2$_1$2$_1$ (#19) |
| Z value | 4 |
| D$_{calc}$ | 1.333 g/cm$^3$ |
| F$_{000}$ | 1008.00 |
| μ(MoKα) | 1.60 cm$^{-1}$ |

EXAMPLE 4

Preparation of Fumarate Salt of GS-7340

GS-7340-02 (V). (Scheme 1) A glass-lined reactor was charged with GS-7340 (IV), (1.294 kg, 2.71 mol), fumaric acid (284 g, 2.44 mol), and acetonitrile (24.6 kg). The mixture was heated to reflux to dissolve the solids, filtered while hot and cooled to 5° C. for 16 hours. The product was isolated by filtration, rinsed with acetonitrile (9.2 kg), and dried to 1329 g (V) as a white powder: mp 119.7-121.1° C.; [α]$_D$$^{20}$ −41.7° (c 1.0, acetic acid).

EXAMPLE 5

Preparation of GS-7120 (VI)

Scheme 3

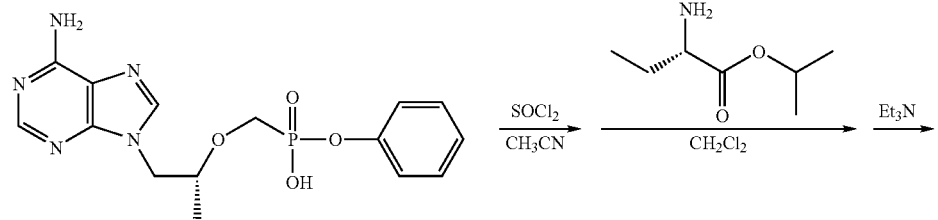

II

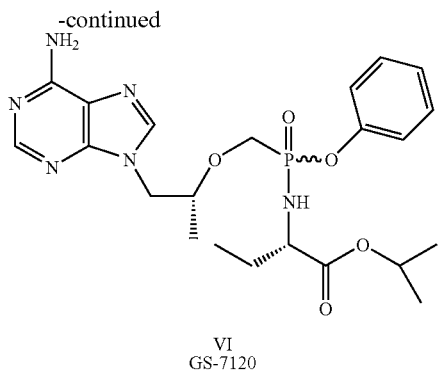

VI
GS-7120

A 5 L round bottom flask was charged with monophenyl PMPA, (II), (200 g, 0.55 mol) and acetonitrile (0.629 kg); Thionyl chloride (0.144 kg, 1.21 mol) was added below 27° C. The mixture was heated at 70° C. until solids dissolved. Volatiles (0.45 L) were removed by atmospheric distillation under nitrogen. The pot residue was cooled to 25° C., dichloromethane (1.6 kg) was added and the mixture was cooled to −20° C. A solution of (L)-α aminobutyric acid ethyl ester (0.144 kg, 1.1 mol) in dichloromethane (1.33 kg) was added over 18 minutes at −20 to −10° C. followed by triethylamine (0.17 kg, 1.65 mol) over 15 minutes at −8 to −15° C. The reaction mixture was warmed to room temperature and washed four times with sodium dihydrogenphosphate solution (10% aq., 0.3 L each wash). The organic solution was dried with anhydrous sodium sulfate (0.5 kg) and filtered. The solids were rinsed with dichloromethane (0.6 kg) and the combined filtrate and rinse was concentrated to an oil under reduced pressure. The oil was purified by chromatography over a 15×13 cm bed of 1.2 kg silica gel 60, 230 to 400 mesh. The column was eluted with a gradient of dichloromethane and methanol. Product bearing fractions were concentrated under reduced pressure to afford 211 g VI (Scheme 3) as a tan foam.

EXAMPLE 5a

Diastereomer Separation of GS-7120 by Batch Elution Chromatography

The diastereomeric mixture was purified using the conditions described for GS-7171 in Example 3A except for the following:
Mobile Phase (Initial): GS-7120-Acetonitrile: Isopropyl Alcohol (98:2)
(Final): 100% Methyl Alcohol
Elution Profile: GS-7341 (diastereomer B)
:GS-7342 (diastereomer A)

EXAMPLE 6

Diastereomer Separation of GS-7120 by Crystallization

A 1 L round bottom flask was charged with monophenyl PMPA, (II), (50 g, 0.137 mol) and acetonitrile (0.2 L). Thionyl chloride (0.036 kg, 0.303 mol) was added with a 10° C. exotherm. The mixture was heated to reflux until solids dissolved. Volatiles (0.1 L) were removed by atmospheric distillation under nitrogen. The pot residue was cooled to 25° C., dichloromethane (0.2 kg) was added, and the mixture was cooled to −20° C. A solution of (L)-α aminobutyric acid ethyl ester (0.036 kg, 0.275 mol) in dichloromethane (0.67 kg) was added over 30 minutes at −20 to −8° C. followed by triethylamine (0.042 kg, 0.41 mol) over 10 minutes at up to −6° C. The reaction mixture was warmed to room temperature and washed four times with sodium dihydrogenphosphate solution (10% aq., 0.075 L each wash). The organic solution was dried with anhydrous sodium sulfate (0.1 kg) and filtered. The solids were rinsed with ethyl acetate (0.25 L, and the combined filtrate and rinse was concentrated to an oil under reduced pressure. The oil was diluted with ethyl acetate (0.25 L), seeded, stirred overnight, and chilled to −15° C. The solids were isolated by filtration and dried under reduced pressure to afford 17.7 g of GS-7342 (Table 5) as a tan powder: $^1$H NMR (CDCl$_3$) δ 0.95 (t, 3H), 1.3 (m, 6H), 1.7, (m, 2H), 3.7 (m, 2H), 4.1(m, 6H), 4.4 (dd, 1H), 5.8 (s, 2H), 7.1 (m, 5H), 8.0 (s, 1H), 8.4 (s, 1H); $^{31}$P NMR (CDCl$_3$) δ 21 (decoupled).

EXAMPLE 7

Diastereomer Separation of GS-7097

The diastereomeric mixture was purified using the conditions described for GS-7171 (Example 3A) except for the following:
Mobile Phase (Initial): GS-7120-Acetonitrile: Isopropyl Alcohol (95:5)
(Final): 100% Methyl Alcohol
Elution Profile: GS-7115 (diastereomer B)
:GS-7114 (diastereomer A)

EXAMPLE 8

Alternative Procedure for Preparation of GS-7097

GS-7097: Phenyl PMPA, Ethyl L-Alanyl Amidate. Phenyl PMPA (15.0 g, 41.3 mmol), L-alanine ethyl ester hydrochloride (12.6 g, 83 mmol) and triethylamine (11.5 mL, 83 mmol) were slurried together in 500 mL pyridine under dry N$_2$. This suspension was combined with a solution of triphenylphosphine (37.9 g, 145 mmol), Aldrithiol 2 (2,2'-dipyridyl disulfide) (31.8 g, 145 mmol), and 120 mL pyridine. The mixture was heated at an internal temperature of 57° C. for 15 hours. The complete reaction was concentrated under vacuum to a yellow paste, 100 g. The paste was purified by column chromatography over a 25×11 cm bed of 1.1 kg silica gel 60, 230 to 400 mesh. The column was eluted with 8 liters of 2% methanol in dichloromethane followed by a linear gradient over a course of 26 liters eluent up to a final composition of 13% methanol. Clean product bearing fractions were concentrated to yield 12.4 g crude (5), 65% theory. This material was contaminated with about 15% (weight) triethylamine hydrochloride by $^1$H NMR. The contamination was removed by dissolving the product in 350 mL ethyl acetate, extracting with 20 mL water, drying the organic solution over anhydrous sodium sulfate, and concentrating to yield 11.1 g pure GS-7097 as a white solid, 58% yield. The process also is employed to synthesize the diastereomeric mixture of GS-7003a and GS-7003b (the phenylalanyl amidate) and the mixture GS-7119 and GS-7335 (the glycyl amidate). These diastereomers are separated using a batch elution procedure such as shown in Example 3A, 6 and 7.

EXAMPLE 9

In Vitro Studies of Prodrug Diastereomers

The in vitro anti-HIV-1 activity and cytotoxicity in MT-2 cells and stability in human plasma and MT-2 cell extracts of GS-7340 (freebase) and tenofovir disoproxil fumarate (TDF), are shown in Table 1. GS-7340 shows a 10-fold increase in antiviral activity relative to TDF and a 200-fold increase in plasma stability. This greater plasma stability is expected to result in higher circulating levels of GS-7340 than TDF after oral administration.

TABLE 1

| | In Vitro Activity and Stability | | | | |
|---|---|---|---|---|---|
| | HIV-1 | | Stability T ½ (min) | | |
| | Activity $IC_{50\,\mu M}$ | Cytotoxicity $CC_{50\,\mu M}$ | Human Plasma | MT-2 Cell Extract | (P/MT-2) |
| GS 7340 | 0.005 | >40 | 90.0 | 28.3 | 3.2 |
| TDF | 0.05 | 70 | 0.41 | 70.7 | 0.006 |
| Tenofovir | 5 | 6000 | — | — | — |

In order to estimate the relative intracellular PMPA resulting from the intracellular metabolism of TDF as compared to that from GS-7340, both prodrugs and PMPA were radiolabeled and spiked into intact human whole blood at equimolar concentrations. After 1 hour, plasma, red blood cells (RBCs) and peripheral blood mononuclear cells (PBMCs) were isolated and analyzed by HPLC with radiometric detection. The results are shown in Table 2.

After 1 hour, GS-7340 results in 10× and 30× the total intracellular concentration of PMPA species in PBMCs as compared to TDF and PMPA, respectively. In plasma after 1 hour, 84% of the radioactivity is due to intact GS-7340, whereas no TDF is detected at 1 hour. Since no intact TDF is detected in plasma, the 10× difference at 1 hour between TDF and GS-7340 is the minimum difference expected in vivo. The HPLC chromatogram for all three compounds in PBMCs is shown in FIG. 1.

TABLE 2

PMPA Metabolites in Plasma, PBMCs and RBCs After 1 h Incubation of PMPA Prodrugs or PMPA in Human Blood.

| Compound | Matrix | Total C-14 Recovered, μg-eq | Metabolites (% of Total Peak Area) | | | | | |
|---|---|---|---|---|---|---|---|---|
| | | | PMPA % | PMPAp, % | PMPApp, % | Met. X, % | Met. Y, % | GS 7340, % |
| GS-7340 | Plasma/FP | 43.0 | 1 | — | — | 2 | 13 | 84 |
| (60 μg-eq) | PBMC | 1.25 | 45 | 16 | 21 | 18 | — | — |
| | RBC/FP | 12.6 | 8 | — | — | 24 | 11 | 57 |
| | | | PMPA | PMPAp | PMPApp | Mono-POC | GS-4331 | |
| GS-4331 | Plasma/FP | 48.1 | 11 | — | — | 89 | — | |
| (TDF) | PBMC | 0.133 | 50 | 25 | 18 | 7 | — | |
| (60 μg-eq) | RBC/FP | 10.5 | 93 | 7.0 | — | — | — | |
| | | | PMPA | PMPAp | PMPApp | | | |
| PMPA | Plasma/FP | 55.7 | 100 | — | — | | | |
| (60 μg-eq) | PBMC | 0.033 | 86 | 14 | — | | | |
| | RBC/FP | 3.72 | 74 | 10 | 16 | | | |

Met. X and Met Y (metabolites X and Y) are shown in Table 5. Lower case "p" designates phosphorylation. These results were obtained after 1 hour in human blood. With increasing time, the in vitro differences are expected to increase, since 84% of GS-7340 is still intact in plasma after one hour. Because intact GS-7340 is present in plasma after oral administration, the relative clinical efficacy should be related to the $IC_{50}$ values seen in vitro.

in Table 3 below, $IC_{50}$ values of tenofovir, TDF, GS-7340, several nucleosides and the protease inhibitor nelfinivir are listed. As shown, nelfinavir and GS-7340 are 2-3 orders of magnitude more potent than all other nucleotides or nucleosides.

TABLE 3

In Vitro Anti-HIV-1 Activities of Antiretroviral Compounds

| Compound | $IC_{50}$ (µM) |
| --- | --- |
| Adefovir (PMEA) | 13.4 ± 4.2[1] |
| Tenofovir (PMPA) | 6.3 ± 3.3[1] |
| AZT | 0.17 ± 0.08[1] |
| 3TC | 1.8 ± 0.25[1] |
| d4T | 8 ± 2.5[1] |
| Nelfinavir | 0.006 ± 0.002[1] |
| TDF | 0.05 |
| GS 7340 | 0.005 |

[1]A. S. Mulato and J. M. Cherrington, Antiviral Research 36, 91 (1997)

Additional studies of the in vitro cell culture anti-HIV-1 activity and $CC_{50}$ of separated diastereomers of this invention were conducted and the results tabulated below.

TABLE 4

Effect of Diastereomer

| Compound | Diastereomer residue | $IC_{50}$ (µM) | Fold change | A/B activity | $CC_{50}$ (µM) |
| --- | --- | --- | --- | --- | --- |
| PMPA | — | 5 | 1× | — | 6000 |
| Ala-methylester | Mixture 1:1 | 0.025 | 200× | 20× | 80 |
| GS-6957a | A | 0.0075 | 670× | | |
| GS-6957b | | 0.15 | 33× | | |
| Phe-methylester | Mixture 1:1 | 0.03 | 170× | 10× | 60 |
| GS-7003a | A | 0.01 | 500× | | |
| GS-7003b | B | 0.1 | 50× | | |
| Gly-ethylester | Mixture 1:1 | 0.5 | 10× | 20× | |
| GS-7119 | A | 0.05 | 100× | | >100 |
| GS-7335 | B | 1.0 | 5× | | |
| Ala-isopropyl | Mixture 1:1 | 0.01 | 500× | 12× | |
| GS-7340 | A | 0.005 | 1,000× | | 40 |
| GS-7339 | B | 0.06 | 83× | | >100 |
| ABA-ethyl | Mixture 1:1 | 0.008 | 625× | 7.5× | >100 |
| GS-7342 | A | 0.004 | 1,250× | | |
| GS-7341 | B | 0.03 | 170× | | |
| Ala-ethyl | Mixture 1:1 | 0.02 | 250× | 10× | 60 |
| GS-7114 | A | 0.005 | 1,000× | | |
| GS-7115 | B | 0.05 | 100× | | |

Assay reference: Arimilli, M N, et al., (1997) Synthesis, in vitro biological evaluation and oral bioavailability of 9-[2-(phosphonomethoxy)propyl]adenine (PMPA) prodrugs. Antiviral Chemistry and Chemotherapy 8(6):557-564.

"Phe-methylester" is the methylphenylalaninyl monoamidate, phenyl monoester of tenofovir; "gly-methylester" is the methylglycyl monoamidate, phenyl monoester of tenofovir.

In each instance above, isomer A is believed to have the same absolute stereochemistry as GS-7340 (S), and isomer B is believed to have the same absolute stereochemistry that of GS-7339.

The in vitro metabolism and stability of separated diastereomers were determined in PLCE, MT-2 extract and human plasma. A biological sample listed below, 80 µL, was transferred into a screw-capped centrifuge tube and incubated at 37° C. for 5 min. A solution containing 0.2 mg/mL of the test compound in a suitable buffer, 20 µL, was added to the biological sample and mixed. The reaction mixture, 20 µL, was immediately sampled and mixed with 60 µL of methanol containing 0.015 mg/mL of 2-hydroxymethylnaphthalene as an internal standard for HPLC analysis. The sample was taken as the time-zero sample. Then, at specific time points, the reaction mixture, 20 µL, was sampled and mixed with 60 µL of methanol containing the internal standard. The mixture thus obtained was centrifuged at 15,000 G for 5 min and the supernatant was analyzed with HPLC under the conditions described below.

The biological samples evaluated are as follows.

(1) PLCE (porcine liver carboxyesterase from Sigma, 160 u/mg protein, 21 mg protein/mL) diluted 20 fold with PBS (phosphated-buffered saline).

(2) MT-2 cell extract was prepared from MT-2 cells according to the published procedure [A. Pompon, I. Lefebvre, J.-L. Imbach, S. Kahn, and D. Farquhar, "Antiviral Chemistry & Chemotherapy", 5:91-98 (1994)] except for using HEPES buffer described below as the medium.

(3) Human plasma (pooled normal human plasma from George King Biomedical Systems, Inc.)

The buffer systems used in the studies are as follows.

In the study for PLCE, the test compound was dissolved in PBS. PBS (phosphate-buffered saline, Sigma) contains 0.01 M phosphate, 0.0027 M potassium chloride, and 0.137 M sodium chloride. pH 7.4 at 37° C.

In the study for MT-2 cell extracts, the test compound was dissolved in HEPES buffer. HEPES buffer contains 0.010 M HEPES, 0.05 M potassium chloride, 0.005 M magnesium chloride, and 0.005 M dl-dithiothreitol. pH 7.4 at 37° C. In the study for human plasma, the test compound was dissolved in TBS. TBS (tris-buffered saline, Sigma) contains 0.05 M Tris, 0.0027 M potassium chloride, and 0.138 M sodium chloride. pH 7.5 at 37° C.

The HPLC analysis was carried out under the following conditions.

Column: Zorbax Rx-C8, 4.6×250 mm, 5µ (MAC-MOD Analytical, Inc. Chadds Ford, Pa.)
Detection: UV at 260 nm
Flow Rate: 1.0 mL/min
Run Time: 30 min
Injection Volume: 20 µL
Column Temperature: Ambient temperature
Mobile Phase A: 50 mM potassium phosphate (pH 6.0)/ $CH_3CN$=95/5 (v/v)
Mobile Phase B: 50 mM Potassium phosphate (pH 6.0)/ $CH_3CN$=50/50 (v/v)
Gradient Run: 0 min 100% Mobile Phase A
  25 min 100% Mobile Phase B
  30 min 100% Mobile Phase B The results are shown below in Table 5 (also including selected $IC_{50}$ data from Table 4).

TABLE 5

In Vitro Metabolism of Isomers A and B of PMPA monoamidate at 37° C.

| No. | PMPA monoamidate structure | HIV IC$_{50}$ (μM) | PLCE hydrolysis rate and product | MT-2 extract hydrolysis rate and product | Human Plasma Stability (HP) |
|---|---|---|---|---|---|
| 1 | 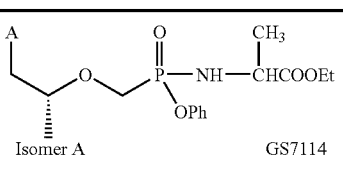 Isomer A  GS7114 | 0.005 | t½ = 2.9 min Met. X & PMPA | t½ = 2.9 min Met. X & PMPA | t½ = 148 min Met. Y |
| 2 | 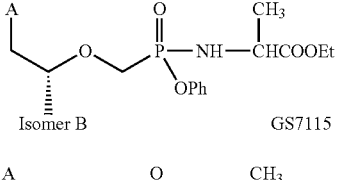 Isomer B  GS7115 | 0.05 | t½ = 8.0 min Met. X & PMPA | t½ = 150.6 min Met. X & PMPA | t½ = 495 min Met. Y |
| 3 | 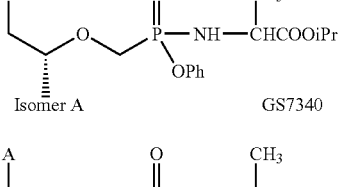 Isomer A  GS7340 | 0.005 | t½ = 3.3 min Met. X & PMPA | t½ = 28.3 min Met. X & PMPA | t½ = 90.0 min Met. Y |
| 4 | 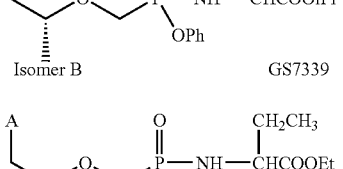 Isomer B  GS7339 | 0.06 | t½ = 10.1 min Met. X & PMPA | t½ > 1000 min | t½ = 231 min Met. Y |
| 5 | 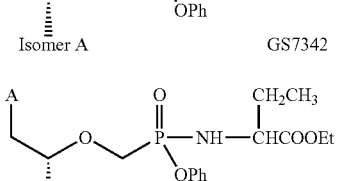 Isomer A  GS7342 | 0.004 | t½ = 3.9 min Met. X | t½ = 49.2 min Met. X & PMPA | t½ = 103 min Met. Y |
| 6 | 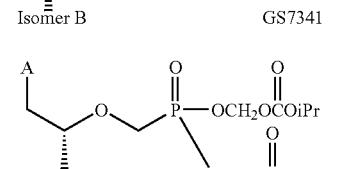 Isomer B  GS7341 | 0.03 | t½ = 11.3 min Met. X | t½ > 1000 min | t½ = 257 min Met. Y |
| 7 | 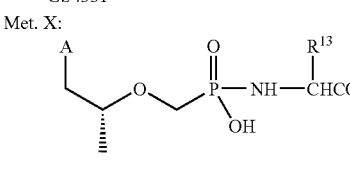 GS4331 | 0.05 | t½ < 0.14 min MonoPOC PMPA | t½ = 70.7 min monoPOC PMPA | t½ = 0.41 min monoPOC PMPA |

Met. X: 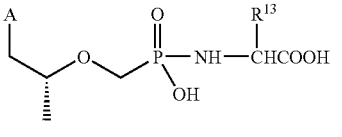

Met. Y: 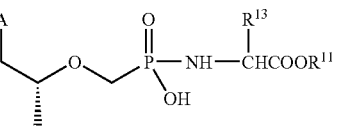

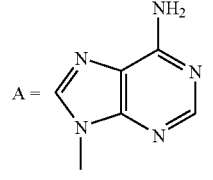

EXAMPLE 10

Plasma and PBMC Exposures Following Oral Administration Of Prodrug Diastereomers to Beagle Dogs The pharmacokinetics of GS 7340 were studied in dogs after oral administration of a 10 mg-eq/kg dose.

Formulations. The prodrugs were formulated as solutions in 50 mM citric acid within 0.5 hour prior to dose. All compounds used in the studies were synthesized by Gilead Sciences. The following lots were used:

| GSI | Amidate Amino acid | AA Ester | Diastereoisomer | Lot Number |
|---|---|---|---|---|
| GS-7340-2 | Alanine | i-Propyl | Isomer A | 1504-187-19 |
| GS-7339 | Alanine | i-Propyl | Isomer B | 1509-185-31 |
| GS7114 | Alanine | Ethyl | Isomer A | 1509-181-26 |
| GS7115 | Alanine | Ethyl | Isomer B | 1509-181-22 |
| GS7119 | Glycine | Ethyl | Isomer A | 1428-163-28 |
| GS7342 | α-Aminobutyric Acid | Ethyl | Isomer A | 1509-191-12 |
| GS7341 | α-Aminobutyric Acid | Ethyl | Isomer B | 1509-191-7 |

Dose Administration and Sample Collection. The in-life phase of this study was conducted in accordance with the recommendations of the "Guide for the Care and Use of Laboratory Animals" (National Institutes of Health publication 86-23) and was approved by an Institutional Animal Care and Use Committee. Fasted male beagle dogs (10±2 kg) were used for the studies. Each drug was administered as a single dose by oral gavage (1.5-2 ml/kg). The dose was 10 mg-equivalent of PMPA/kg. For PBMCs, blood samples were collected at 0 (pre-dose), 2, 8, and 24 h post-dose. For plasma, blood samples were collected at 0 (pre-dose), 5, 15, and 30 min, and 1, 2, 3, 4, 6, 8, 12 and 24 h post-dose. Blood (1.0 ml) was processed immediately for plasma by centrifugation at 2,000 rpm for 10 min. Plasma samples were frozen and maintained at 70° C. until analyzed.

Peripheral Blood Mononuclear Cell (PBMC) preparation. Whole blood (8 ml) drawn at specified time points was mixed in equal proportion with phosphate buffered saline (PBS), layered onto 15 ml of Ficoll-Paque solution (Pharmacia Biotech,) and centrifuged at 400×g for 40 min. PBMC layer was removed and washed once with PBS. Formed PMBC pellet was reconstituted in 0.5 ml of PBS, cells were resuspended, counted using hemocytometer and maintained at 70° C. until analyzed. The number of cells multiplied by the mean single-cell volume was used in calculation of intracellular concentrations. A reported value of 200 femtoliters/cell was used as the resting PBMC volume (B. L. Robins, R. V. Srinivas, C. Kim, N. Bischofberger, and A. Fridland, Antimicrob. Agents Chemother. 42, 612 (1998).

Determination of PMPA and Prodrugs in plasma and PBMCs. The concentration of PMPA in dog plasma samples was determined by derivatizing PMPA with chloroacetaldehyde to yield a highly fluorescent $N^1$, $N^6$-ethenoadenine derivative (L. Naesens, J. Balzarini, and E. De Clercq, Clin. Chem. 38, 480 (1992). Briefly, plasma (100 μl) was mixed with 200 μl acetonitrile to precipitateprotein. Samples were then evaporated to dryness under reduced pressure at room temperature. Dried samples were reconstituted in 200 μl derivatization cocktail (0.34% chloroacetaldehyde in 100 mM sodium acetate, pH 4.5), vortexed, and centrifuged. Supernatant was then transferred to a clean screw-cap tube and incubated at 95° C. for 40 min. Derivatized samples were then evaporated to dryness and reconstituted in 100 μl of water for HPLC analysis.

Before intracellular PMPA could be determined by HPLC, the large amounts of adenine related ribonucleotides present in the PBMC extracts had to be removed by selective oxidation. We used a modified procedure of Tanaka et al (K. Tanaka, A. Yoshioka, S. Tanaka, and Y. Wataya, Anal. Biochem., 139, 35 (1984). Briefly, PBMC samples were mixed 1:2 with methanol and evaporated to dryness under reduced pressure. The dried samples were derivatized as described in the plasma assay. The derivatized samples were mixed with 20 μL of 1M rhamnose and 30 μL of 0.1M sodium periodate and incubated at 37° C. for 5 min. Following incubation, 40 μL of 4M methylamine and 20 μL of 0.5M inosine were added. After incubation at 37° C. for 30 min, samples were evaporated to dryness under reduced pressure and reconstituted in water for HPLC analysis.

No intact prodrug was detected in any PBMC samples. For plasma samples potentially containing intact prodrugs, experiments were performed to verify that no further conversion to PMPA occurred during derivatization. Prodrug standards were added to drug-free plasma and derivatized as described. There were no detectable levels of PMPA present in any of the plasma samples, and the projected % of conversion was less than 1%.

The HPLC system was comprised of a P4000 solvent delivery system with AS3000 autoinjector and F2000 fluorescence detector (Thermo Separation, San Jose, Calif.). The column was an Inertsil ODS-2 column (4.6×150 mm). The mobile phases used were: A, 5% acetonitrile in 25 mM potassium phosphate buffer with 5 mM tetrabutyl ammonium bromide (TBABr), pH 6.0; B, 60% acetonitrile in 25 mM potassium phosphate buffer with 5 mM TBABr, pH 6.0. The flow rate was 2 ml/min and the column temperature was maintained at 35° C. by a column oven. The gradient profile was 90% A/10% B for 10 min for PMPA and 65% A/35% B for 10 min for the prodrug. Detection was by fluorescence with excitation at 236 nm and emission at 420 nm, and the injection volume was 10 μl. Data was acquired and stored by a laboratory data acquisition system (PeakPro, Beckman, Allendale, N.J.).

Pharmacokinetic Calculations. PMPA and prodrug exposures were expressed as areas under concentration curves in plasma or PBMC from zero to 24 hours (AUC). The AUC values were calculated using the trapezoidal rule.

Plasma and PBMC Concentrations. The results of this study is shown in FIGS. 2 and 3. FIG. 2 shows the time course of GS 7340-2 metabolism summary of plasma and PBMC exposures following oral administration of pure diastereoisomers of the PMPA prodrugs.

The bar graph in FIG. 2 shows the AUC (0-24 h) for tenofovir in dog PBMCs and plasma after administration of PMPA s.c., TDF and amidate ester prodrugs. All of the amidate prodrugs exhibited increases in PBMC exposure. For example, GS 7340 results in a ~21-fold increase in PBMC exposure as compared to PMPA s.c. and TDF; and a 6.25-fold and 1.29-fold decrease in plasma exposure, respectively.

These data establish in vivo that GS 7340 can be delivered orally, minimizes systemic exposure to PMPA and greatly enhances the intracellular concentration of PMPA in the cells primarily responsible for HIV replication.

TABLE 6

PMPA Exposure in PBMC and Plasma from Oral Prodrugs of PMPA in Dogs

| GS# | Moiety | PMPA AUC in Plasma Mean | StDev | N | PMPA AUC in PBMC Mean | StDev | N | Prodrug in Plasma | PBMC/Plasma Exposure Ratio |
|---|---|---|---|---|---|---|---|---|---|
| GS-7114 | Mono-Ala-Et-A | 5.8 | 0.9 | 2 | 706 | 331 | 5 | YES | 122 |
| GS-7115 | Mono-Ala-Et-B | 6.6 | 1.5 | 2 | 284 | 94 | 5 | YES | 43 |
| GS-7340-2 | Mono-Ala-iPr-A | 5.0 | 1.1 | 5 | 805 | 222 | 5 | YES | 161 |
| GS-7339 | Mono-Ala-iPr-A | 6.4 | 1.3 | 2 | 200 | 57 | 5 | YES | 31 |
| GS-7119 | Mono-Gly-Et-A | 6.11 | 1.86 | 2 | 530 | 304 | 5 | YES | 87 |
| GS-7342 | Mono-ABA-Et-A | 4.6 | 1.2 | 2 | 1060 | 511 | 5 | YES | 230 |
| GS7341 | Mono-ABA-Et-B | 5.8 | 1.4 | 2 | 199 | 86 | 5 | YES | 34 |

EXAMPLE 11

Biodistribution of GS-7340

As part of the preclinical characterization of GS-7340, its biodistribution in dogs was determined. The tissue distribution of GS-7340 (isopropyl alaninyl monoamidate, phenyl monoester of tenofovir) was examined following oral administration to beagle dogs. Two male animals were dosed orally with $^{14}C$=GS-7340 (8.85 mg-equiv. of PMPA/kg, 33.2 µCi/kg; the 8-carbon of adenine is labeled) in an aqueous solution (50 mM citric acid, pH 2.2). Plasma and peripheral blood mononuclear cells (PBMCs) were obtained over the 24-hr period. Urine and feces were cage collected over 24 hr. At 24 h after the dose, the animals were sacrificed and tissues removed for analysis. Total radioactivity in tissues was determined by oxidation and liquid scintillation counting.

The biodistribution of PMPA after 24 hours after a single oral dose of radiolabelled GS 7340 is shown in Table 4 along with the data from a previous study with TDF (GS-4331). In the case of TDF, the prodrug concentration in the plasma is below the level of assay detection, and the main species observed in plasma is the parent drug. Levels of PMPA in the lymphatic tissues, bone marrow, and skeletal muscle are increased 10-fold after administration of GS-7340.

Accumulation in lymphatic tissues is consistent with the data observed from the PBMC analyses, since these tissues are composed primarily of lymphocytes. Likewise, accumulation in bone marrow is probably due to the high percentage of lymphocytes (70%) in this tissue.

TABLE 7

Excretion and Tissue Distribution of Radiolabelled GS-7340 in Dogs (Mean, N = 2) Following an Oral Dose at 10 mg-eq. PMPA/kg.

| Tissue/Fluid | GS-4331 % Dose | Conc. (ug-eq/g) | GS-7340 % Dose | Conc. (ug-eq/g) | Tissue Conc. Ratio of GS 7340 to GS-4331 |
|---|---|---|---|---|---|
| Liver | 12.40 | 38.30 | 16.45 | 52.94 | 1.4 |
| Kidney | 4.58 | 87.90 | 3.78 | 80.21 | 0.9 |
| Lungs | 0.03 | 0.53 | 0.34 | 4.33 | 8.2 |
| Iliac Lymph Nodes | 0.00 | 0.51 | 0.01 | 5.42 | 10.6 |
| Axillary Lymph Nodes | 0.00 | 0.37 | 0.01 | 5.54 | 14.8 |
| Inguinal Lymph Nodes | 0.00 | 0.28 | 0.00 | 4.12 | 15.0 |
| Mesenteric Lymph Nodes | 0.00 | 1.20 | 0.04 | 6.88 | 5.7 |
| Thyroid Gland | 0.00 | 0.30 | 0.00 | 4.78 | 15.8 |
| Pituitary Gland | 0.00 | 0.23 | 0.00 | 1.80 | 7.8 |
| Salivary Gland (L + R) | 0.00 | 0.45 | 0.03 | 5.54 | 12.3 |
| Adrenal Gland | 0.00 | 1.90 | 0.00 | 3.47 | 1.8 |
| Spleen | 0.00 | 0.63 | 0.17 | 8.13 | 12.8 |
| Pancreas | 0.00 | 0.57 | 0.01 | 3.51 | 6.2 |
| Prostate | 0.00 | 0.23 | 0.00 | 2.14 | 9.1 |
| Testes (L + R) | 0.02 | 1.95 | 0.02 | 2.01 | 1.0 |
| Skeletal Muscle | 0.00 | 0.11 | 0.01 | 1.12 | 10.1 |
| Heart | 0.03 | 0.46 | 0.15 | 1.97 | 4.3 |
| Femoral Bone | 0.00 | 0.08 | 0.00 | 0.28 | 3.5 |
| Bone Marrow | 0.00 | 0.20 | 0.00 | 2.05 | 10.2 |
| Skin | 0.00 | 0.13 | 0.00 | 0.95 | 7.2 |
| Abdominal fat | 0.00 | 0.16 | 0.00 | 0.90 | 5.8 |
| Eye (L + R) | 0.00 | 0.06 | 0.00 | 0.23 | 3.7 |
| Brain | 0.00 | <LOD | 0.00 | <LOD | n.d. |
| Cerebrospinal Fluid | 0.00 | <LOD | 0.00 | 0.00 | n.d. |
| Spinal Cord | 0.00 | <LOD | 0.00 | 0.04 | n.d. |
| Stomach | 0.11 | 1.92 | 0.26 | 2.68 | 1.4 |
| Jejunum | 1.34 | 3.01 | 0.79 | 4.16 | 1.4 |
| Duodenum | 0.49 | 4.96 | 0.44 | 8.77 | 1.8 |
| Ileum | 0.01 | 0.50 | 0.16 | 4.61 | 9.2 |
| Large Intestine | 1.63 | 5.97 | 2.65 | 47.20 | 7.9 |
| Gall bladder | 0.00 | 3.58 | 0.04 | 25.02 | 7.0 |

TABLE 7-continued

Excretion and Tissue Distribution of Radiolabelled GS-7340 in Dogs (Mean, N = 2) Following an Oral Dose at 10 mg-eq. PMPA/kg.

| Tissue/Fluid | GS-4331 % Dose | GS-4331 Conc. (ug-eq/g) | GS-7340 % Dose | GS-7340 Conc. (ug-eq/g) | Tissue Conc. Ratio of GS 7340 to GS-4331 |
|---|---|---|---|---|---|
| Bile | 0.00 | 9.63 | 0.22 | 40.48 | 4.2 |
| Feces | 40.96 | n.d. | 0.19 | n.d. | n.a. |
| Total GI Tract Contents | 5.61 | n.d. | 21.64 | n.d. | n.a. |
| Urine | 23.72 | n.d. | 14.73 | n.d. | n.a. |
| Plasma at 24 h | 0.00 | 0.20 | 0.00 | 0.20 | 1.0 |
| Plasma at 0.25 h | n.a. | 3.68 | n.a. | 3.48 | 0.9 |
| PBMC* | 0.00 | n.d. | 0.00 | 63.20 | n.d. |
| Whole Blood | 0.00 | 0.85 | 0.16 | 0.20 | 0.2 |
| Total Recovery | 81.10 | | 68.96 | | |

Calculated using typical recovery of $15 \times 10^6$ cells total, and mean PBMC volume of 0.2 picoliters/cell
n.s. = no sample,
n.a. = not applicable,
n.d. = not determined.

The invention claimed is:

1. A diastereomerically enriched compound having the structure (3)

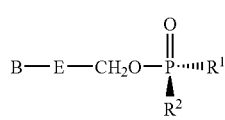

(3)

which contains less than 40% by weight of the diastereomer (4)

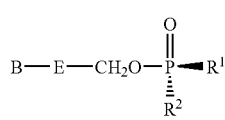

(4)

wherein
$R^1$ is an oxyester which is hydrolyzable in vivo, or hydroxyl;
B is a heterocyclic base;
$R^2$ is hydroxyl, or the residue of an amino acid bonded to the P atom through an amino group of the amino acid and having each carboxy substituent of the amino acid optionally esterified, but not both of $R^1$ and $R^2$ are hydroxyl;
E is —(CH$_2$)$_2$—, —CH(CH$_3$)CH$_2$—, —CH(CH$_2$F)CH$_2$—, —CH(CH$_2$OH)CH$_2$—, —CH(CH=CH$_2$)CH$_2$—, —CH(C≡CH)CH$_2$—, —CH(CH$_2$N$_3$)CH$_2$—,

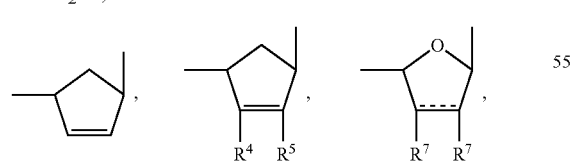

—CH($R^6$)OCH($R^6$)—, —CH($R^9$)CH$_2$O— or —CH($R^8$)O—, wherein the right hand bond is linked to the heterocyclic base;
the broken line represents an optional double bond;
$R^4$ and $R^5$ are independently hydrogen, hydroxy, halo, amino or a substituent having 1-5 carbon atoms selected from acyloxy, alkyoxy, alkylthio, alkylamino and dialkylamino;

$R^6$ and $R^{6'}$ are independently H, $C_1$-$C_6$ alkyl, $C_1$-$C_6$ hydroxyalkyl, or $C_2$-$C_7$ alkanoyl;
$R^7$ is independently H, $C_1$-$C_6$ alkyl, or are taken together to form —O— or —CH$_2$—;
$R^8$ is H, $C_1$-$C_6$ alkyl, $C_1$-$C_6$ hydroxyalkyl or $C_1$-$C_6$ haloalkyl; and
$R^9$ is H, hydroxymethyl or acyloxymethyl;
and their salts, free base, and solvates.

2. The compound of claim 1 containing less than 20% by weight of the diastereomer (4).

3. The compound of claim 1 containing less than 5% by weight of the diastereomer (4).

4. A diastereomerically enriched compound having the structure (5a)

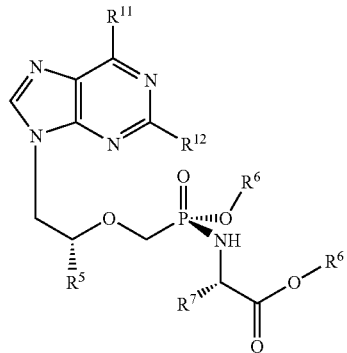

(5a)

which contains less than 40% by weight of diastereomer (5b)

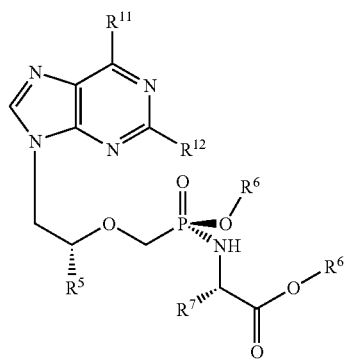

(5b)

wherein

R⁵ is methyl or hydrogen;

R⁶ independently is H, alkyl, alkenyl, alkynyl, aryl or arylalkyl, or R⁶ independently is alkyl, alkenyl, alkynyl, aryl or arylalkyl which is substituted with from 1 to 3 substituents selected from alkylamino, alkylaminoalkyl, dialkylaminoalkyl, dialkylamino, hydroxyl, oxo, halo, amino, alkylthio, alkoxy, alkoxyalkyl, aryloxy, aryloxyalkyl, arylalkoxy, arylalkoxyalkyl, haloalkyl, nitro, nitroalkyl, azido, azidoalkyl, alkylacyl, alkylacylalkyl, carboxyl, or alkylacylamino;

R⁷ is the side chain of any naturally-occurring or pharmaceutically acceptable amino acid and which, if the side chain comprises carboxyl, the carboxyl group is optionally esterified with an alkyl or aryl group;

R¹¹ is amino, alkylamino, oxo, or dialkylamino; and

R¹² is amino or H;

and its salts, tautomers, free base and solvates.

5. The compound of claim 4 containing less than 20% by weight of the diastereomer (5b).

6. The compound of claim 4 containing less than 5% by weight of the diastereomer (5b).

7. A diastereomerically enriched compound of structure (6)

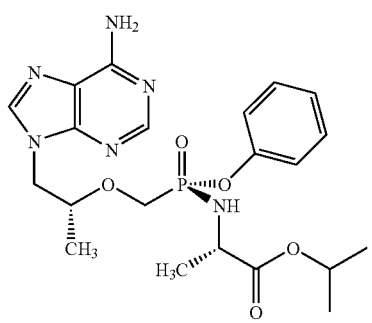

(6)

and its salts, tautomers, free base and solvates.

8. A diastereomerically enriched compound of structure (7)

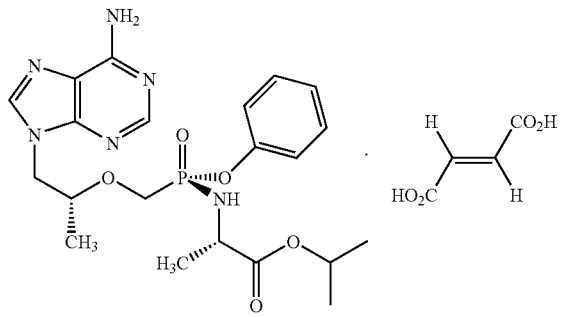

(7)

which contains less than 40% of diastereomer (7a)

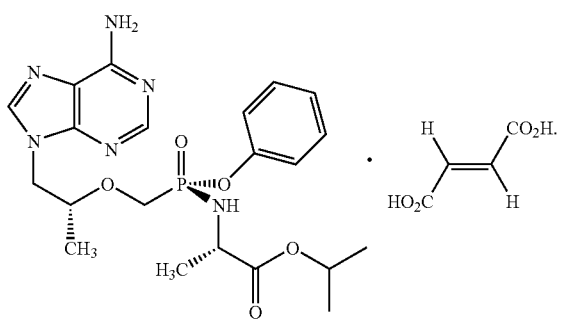

(7a)

9. The compound of claim 8 containing less than 20% by weight of the diastereomer (7a).

10. The compound of claim 8 containing less than 5% by weight of the diastereomer (7a).

11. A composition comprising a compound of any of claims 1-8 or 2-10 and a pharmaceutically effective excipient.

12. The composition of claim 11 wherein the excipient is a gel.

13. The composition of claim 11 which is suitable for topical administration.

* * * * *

UNITED STATES PATENT AND TRADEMARK OFFICE
CERTIFICATE OF CORRECTION

PATENT NO. : 7,390,791 B2
APPLICATION NO. : 10/798692
DATED : June 24, 2008
INVENTOR(S) : Mark W. Becker et al.

It is certified that error appears in the above-identified patent and that said Letters Patent is hereby corrected as shown below:

ON THE TITLE PAGE [56] REFERENCES CITED:

Foreign Patent Documents, "WO 0208241 A2*" should read --WO 02/08241 A2*--.

COLUMN 3:

Line 17, "alkyoxy" should read --alkyloxy--.

COLUMN 5:

Line 8, "Dogs" should read --dogs--.

COLUMN 8:

Line 19, "possess" should read --possesses--.

COLUMN 10:

Line 10, "therefore." should read --therefor.--.

COLUMN 11:

Line 16, "$R_{22}$;" should read --$R^{22}$;--.

COLUMN 12:

Line 48, "1-dezazadenyl," should read --l-dezaadenyl,--.

COLUMN 13:

Line 4, "$C_6$-$C_1$" should read --$C_6$-$C_{15}$--.

Signed and Sealed this
Nineteenth Day of March, 2013

Teresa Stanek Rea
*Acting Director of the United States Patent and Trademark Office*

COLUMN 21:

Line 61, "a oil." should read --an oil.--.

COLUMN 23:

Line 8, "minute" should read --minutes--.

COLUMN 29:

Line 1, "Met Y" should read --Met. Y--;
   Line 10, "in Table 3" should read --In Table 3--;
   Line 11, "nelfinivir" should read --nelfinavir--; and
   Line 59, "Arimilli, M N," should read --Arimilli, MN,--.

COLUMN 30:

Line 3, "that of" should read --as that of--; and
   Line 51, "Rx-C8," should read --Rx-C$_8$,--.

COLUMN 33:

Line 63, "precipitateprotein." should read --precipitate protein.--.

COLUMN 34:

Line 53, "is shown" should read --are shown--.

COLUMN 37:

Line 66, "alkyoxy" should read --alkyloxy--.

COLUMN 40:

Lines 21-32,

"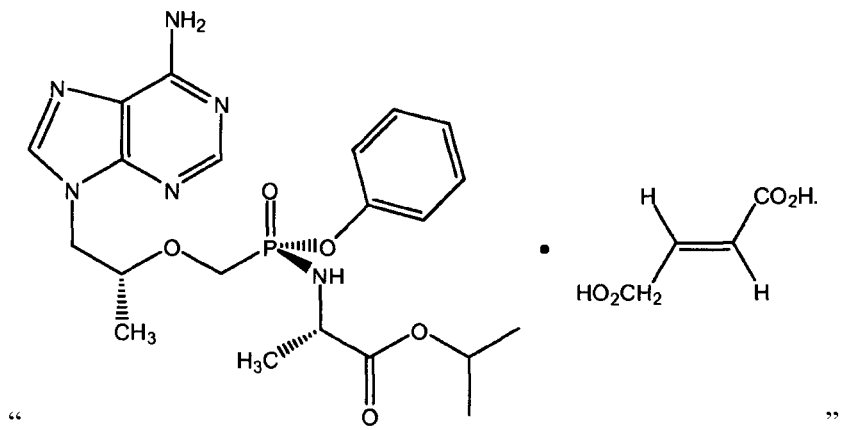"

should read
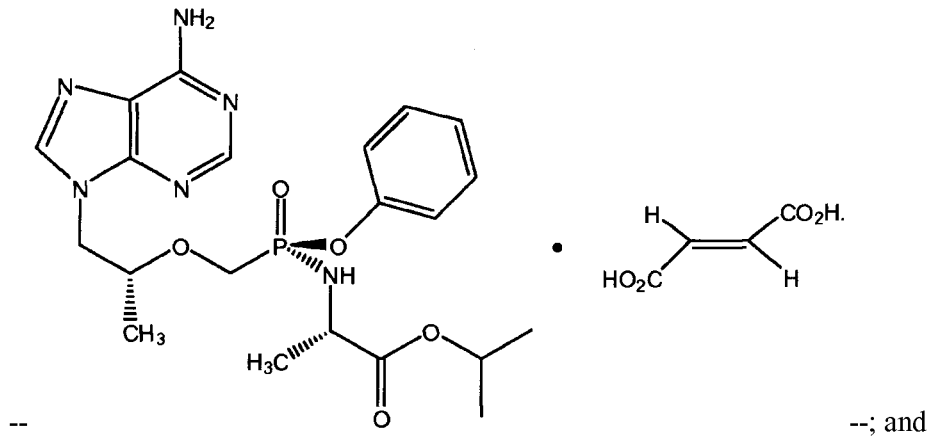
-- --; and
Line 39, "claims 1-8 or 2-10" should read --claims 1-10--.